US011081208B2

(12) United States Patent
Jaffe et al.

(10) Patent No.: US 11,081,208 B2
(45) Date of Patent: Aug. 3, 2021

(54) SYSTEMS, METHODS, AND MEDIA FOR DE NOVO ASSEMBLY OF WHOLE GENOME SEQUENCE DATA

(71) Applicant: 10X GENOMICS, INC., Pleasanton, CA (US)

(72) Inventors: David Jaffe, Pleasanton, CA (US); Patrick Marks, San Francisco, CA (US); Michael Schnall-Levin, San Francisco, CA (US); Neil Weisenfeld, North Reading, MA (US)

(73) Assignee: 10X GENOMICS, INC., Pleasanton, CA (US)

( * ) Notice: Subject to any disclaimer, the term of this patent is extended or adjusted under 35 U.S.C. 154(b) by 560 days.

(21) Appl. No.: 15/242,256

(22) Filed: Aug. 19, 2016

(65) Prior Publication Data

US 2017/0235876 A1    Aug. 17, 2017

Related U.S. Application Data

(60) Provisional application No. 62/294,184, filed on Feb. 11, 2016, provisional application No. 62/332,914, filed on May 6, 2016.

(51) Int. Cl.
*G01N 33/48* (2006.01)
*G01N 33/50* (2006.01)
*G16B 30/00* (2019.01)

(52) U.S. Cl.
CPC .................................. *G16B 30/00* (2019.02)

(58) Field of Classification Search
CPC ................................ G16B 30/00; G16B 30/20
See application file for complete search history.

(56) References Cited

U.S. PATENT DOCUMENTS

| | | |
|---|---|---|
| 4,124,638 A | 11/1978 | Hansen |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,436,130 A | 7/1995 | Mathies et al. |
| 5,478,893 A | 12/1995 | Ghosh et al. |
| 5,512,131 A | 4/1996 | Kumar et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,736,330 A | 4/1998 | Fulton |
| 5,756,334 A | 5/1998 | Perler et al. |
| 5,834,197 A | 11/1998 | Parton |
| 5,846,719 A | 12/1998 | Brenner et al. |
| 5,851,769 A | 12/1998 | Gray et al. |
| 5,856,174 A | 1/1999 | Lipshutz et al. |
| 5,900,481 A | 5/1999 | Lough et al. |
| 5,942,609 A | 8/1999 | Hunkapiller et al. |
| 5,958,703 A | 9/1999 | Dower et al. |
| 5,994,056 A | 11/1999 | Higuchi |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,123,798 A | 9/2000 | Gandhi et al. |
| 6,143,496 A | 11/2000 | Brown et al. |
| 6,171,850 B1 | 1/2001 | Nagle et al. |
| 6,172,218 B1 | 1/2001 | Brenner |
| 6,176,962 B1 | 1/2001 | Soane et al. |
| 6,297,006 B1 | 10/2001 | Drmanac et al. |
| 6,297,017 B1 | 10/2001 | Schmidt et al. |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |

(Continued)

FOREIGN PATENT DOCUMENTS

| | | |
|---|---|---|
| EP | 0249007 A2 | 12/1987 |
| EP | 0637996 B1 | 7/1997 |

(Continued)

OTHER PUBLICATIONS

Abate, et al. Beating Poisson encapsulation statistics using close-packed ordering. Lab Chip. Sep. 21, 2009;9(18):2628-31. doi: 10.1039/b909386a. Epub Jul. 28, 2009.

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.

Abate et al., Valve-based flow focusing for drog formation. Appl Phys Lett. 2009;94. 3 pages.

Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.

(Continued)

*Primary Examiner* — Russell S Negin
(74) *Attorney, Agent, or Firm* — Wilson Sonsini Goodrich & Rosati

(57) ABSTRACT

Described are computer-implemented methods, systems, and media for de novo phased diploid assembly of nucleic acid sequence data generated from a nucleic acid sample of an individual utilizing nucleic acid tags to preserve long-range sequence context for the individual such that a subset of short-read sequence data derived from a common starting sequence shares a common tag. The phased diploid assembly is achieved without alignment to a reference sequence derived from organisms other than the individual. The methods, systems, and media described are computer-resource efficient, allowing scale-up.

29 Claims, 9 Drawing Sheets

Specification includes a Sequence Listing.

(56) References Cited

U.S. PATENT DOCUMENTS

| | | |
|---|---|---|
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,913,935 B1 | 7/2005 | Thomas |
| 6,915,679 B2 | 7/2005 | Chien et al. |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,622,076 B2 | 11/2009 | Davies et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,745,178 B2 | 6/2010 | Dong |
| 7,772,287 B2 | 8/2010 | Higuchi et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,053,192 B2 | 11/2011 | Bignell et al. |
| 8,067,159 B2 | 11/2011 | Brown et al. |
| 8,133,719 B2 | 3/2012 | Drmanac et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,337,778 B2 | 12/2012 | Stone et al. |
| 8,592,150 B2 | 11/2013 | Drmanac et al. |
| 8,603,749 B2 | 12/2013 | Gillevet |
| 8,658,430 B2 | 2/2014 | Miller et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,370 B2 | 4/2015 | Hong |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,764,322 B2 | 9/2017 | Hiddessen et al. |
| 9,824,068 B2 | 11/2017 | Wong et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,059,989 B2 | 8/2018 | Giresi et al. |
| 10,119,167 B2 | 11/2018 | Srinivasan et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 2001/0020588 A1 | 9/2001 | Adourian et al. |
| 2001/0044109 A1 | 11/2001 | Mandecki |
| 2002/0005354 A1 | 1/2002 | Spence et al. |
| 2002/0034737 A1 | 3/2002 | Drmanac |
| 2002/0051971 A1 | 5/2002 | Stuelpnagel et al. |
| 2002/0051992 A1 | 5/2002 | Bridgham et al. |
| 2002/0089100 A1 | 7/2002 | Kawasaki |
| 2002/0092767 A1 | 7/2002 | Bjornson et al. |
| 2002/0119455 A1 | 8/2002 | Chan |
| 2002/0127736 A1 | 9/2002 | Chou et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0027221 A1 | 2/2003 | Scott et al. |
| 2003/0028981 A1 | 2/2003 | Chandler et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |

(56) References Cited

U.S. PATENT DOCUMENTS

| | | |
|---|---|---|
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0042419 A1 | 2/2007 | Barany et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0154903 A1 | 7/2007 | Marla et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0196397 A1 | 8/2007 | Torii et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0056948 A1 | 3/2008 | Dale et al. |
| 2008/0166720 A1 | 7/2008 | Hsieh et al. |
| 2008/0213766 A1 | 9/2008 | Brown et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0047713 A1 | 2/2009 | Handique |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0118488 A1 | 5/2009 | Drmanac et al. |
| 2009/0131543 A1 | 5/2009 | Weitz et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155563 A1 | 6/2009 | Petsev et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0235990 A1 | 9/2009 | Beer |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0184928 A1 | 7/2010 | Kumacheva |
| 2010/0210479 A1 | 8/2010 | Griffiths et al. |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0033854 A1 | 2/2011 | Drmanac et al. |
| 2011/0053798 A1 | 3/2011 | Hindson et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0196288 A1 | 8/2012 | Beer et al. |
| 2012/0211084 A1 | 8/2012 | Weitz et al. |
| 2012/0219947 A1 | 8/2012 | Yurkovetsky et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0309002 A1 | 12/2012 | Link |
| 2012/0316074 A1 | 12/2012 | Saxonov |
| 2013/0028812 A1 | 1/2013 | Prieto et al. |
| 2013/0046030 A1 | 2/2013 | Rotem et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0185096 A1 | 7/2013 | Giusti et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0225418 A1 | 8/2013 | Watson |
| 2013/0268206 A1 | 10/2013 | Porreca et al. |

(56) References Cited

U.S. PATENT DOCUMENTS

| | | |
|---|---|---|
| 2013/0274117 A1 | 10/2013 | Church et al. |
| 2013/0311106 A1 | 11/2013 | White et al. |
| 2013/0317755 A1 | 11/2013 | Mishra et al. |
| 2014/0037514 A1 | 2/2014 | Stone et al. |
| 2014/0057799 A1 | 2/2014 | Johnson et al. |
| 2014/0065234 A1 | 3/2014 | Shum et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0200166 A1 | 7/2014 | Van Rooyen et al. |
| 2014/0206554 A1 | 7/2014 | Hindson et al. |
| 2014/0214334 A1 | 7/2014 | Plattner et al. |
| 2014/0221239 A1 | 8/2014 | Carman et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0272996 A1 | 9/2014 | Bemis |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0323316 A1 | 10/2014 | Drmanac et al. |
| 2014/0338753 A1 | 11/2014 | Sperling et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0066385 A1 | 3/2015 | Schnall-Levin et al. |
| 2015/0111256 A1 | 4/2015 | Church et al. |
| 2015/0133344 A1 | 5/2015 | Shendure et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0267191 A1 | 9/2015 | Steelman et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0353999 A1 | 12/2015 | Agresti et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0314242 A1 | 10/2016 | Schnall-Levin et al. |
| 2016/0348093 A1 | 12/2016 | Price et al. |
| 2016/0350478 A1 | 12/2016 | Chin et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0183701 A1 | 6/2017 | Agresti et al. |
| 2017/0260584 A1 | 9/2017 | Zheng et al. |
| 2018/0030515 A1 | 2/2018 | Regev et al. |
| 2018/0071695 A1 | 3/2018 | Weitz et al. |
| 2018/0080075 A1 | 3/2018 | Brenner et al. |
| 2018/0105808 A1 | 4/2018 | Mikkelsen et al. |
| 2018/0196781 A1 | 7/2018 | Wong et al. |
| 2018/0265928 A1 | 9/2018 | Schnall-Levin et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0371545 A1 | 12/2018 | Wong et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0020417 A1 | 1/2020 | Schnall-Levin et al. |
| 2020/0032335 A1 | 1/2020 | Alvarado Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |

FOREIGN PATENT DOCUMENTS

| | | |
|---|---|---|
| EP | 1019496 B1 | 9/2004 |
| EP | 1482036 B1 | 10/2007 |
| EP | 1841879 A2 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 B1 | 4/2017 |
| GB | 2097692 A | 11/1982 |
| GB | 2097692 B | 5/1985 |
| GB | 2485850 A | 5/2012 |
| JP | S5949832 A | 3/1984 |
| JP | 2006507921 A | 3/2006 |
| JP | 2006289250 A | 10/2006 |
| JP | 2007268350 A | 10/2007 |
| JP | 2009208074 A | 9/2009 |
| JP | 2012525147 A | 10/2012 |
| RU | 2321638 C2 | 4/2008 |
| WO | WO-84/02000 | 5/1984 |
| WO | WO-95/30782 | 11/1995 |
| WO | WO-9629629 A2 | 9/1996 |
| WO | WO-9641011 A1 | 12/1996 |
| WO | WO-9909217 A1 | 2/1999 |
| WO | WO-99/52708 | 10/1999 |
| WO | WO-9952708 A1 | 10/1999 |
| WO | WO-0008212 A1 | 2/2000 |
| WO | WO-2000008212 A1 | 2/2000 |
| WO | WO-0026412 A1 | 5/2000 |
| WO | WO-2001002850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0231203 A2 | 4/2002 |
| WO | WO-02086148 A1 | 10/2002 |
| WO | WO-2004002627 A2 | 1/2004 |
| WO | WO-2004010106 A2 | 1/2004 |
| WO | WO-2004065617 A2 | 8/2004 |

(56) References Cited

FOREIGN PATENT DOCUMENTS

| | | |
|---|---|---|
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006040551 A2 | 4/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007024840 A2 | 3/2007 |
| WO | WO-2007081385 A2 | 7/2007 |
| WO | WO-2007081387 A1 | 7/2007 |
| WO | WO-2007089541 A2 | 8/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009023821 A1 | 2/2009 |
| WO | WO-2009061372 A1 | 5/2009 |
| WO | WO-2009085215 A1 | 7/2009 |
| WO | WO-2009152928 A2 | 12/2009 |
| WO | WO-2010004018 A2 | 1/2010 |
| WO | WO-2010033200 A2 | 3/2010 |
| WO | WO-2010104604 A1 | 9/2010 |
| WO | WO-2010115154 A1 | 10/2010 |
| WO | WO-2010117620 A2 | 10/2010 |
| WO | WO-2010126614 A2 | 11/2010 |
| WO | WO-2010127304 A2 | 11/2010 |
| WO | WO-2010148039 A2 | 12/2010 |
| WO | WO-2010151776 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2012012037 A1 | 1/2012 |
| WO | WO-2012048341 A1 | 4/2012 |
| WO | WO-2012055929 A1 | 5/2012 |
| WO | WO-2012061832 A1 | 5/2012 |
| WO | WO-2012083225 A2 | 6/2012 |
| WO | WO-2012100216 A2 | 7/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013035114 A1 | 3/2013 |
| WO | WO-2013036929 A1 | 3/2013 |
| WO | WO-2013055955 A1 | 4/2013 |
| WO | WO-2013096643 A1 | 6/2013 |
| WO | WO-2013123125 A1 | 8/2013 |
| WO | WO-2013126741 A1 | 8/2013 |
| WO | WO-2013177220 A1 | 11/2013 |
| WO | WO-2014028378 A2 | 2/2014 |
| WO | WO-2014028537 A1 | 2/2014 |
| WO | WO-2014093676 A1 | 6/2014 |
| WO | WO-2014108810 A2 | 7/2014 |
| WO | WO-2014165559 A2 | 10/2014 |
| WO | WO-2015015199 A2 | 2/2015 |
| WO | WO-2015044428 A1 | 4/2015 |
| WO | WO-2015157567 A1 | 10/2015 |
| WO | WO-2015164212 A1 | 10/2015 |
| WO | WO-2015200891 A1 | 12/2015 |
| WO | WO-2016040476 A1 | 3/2016 |
| WO | WO-2016061517 A2 | 4/2016 |
| WO | WO-2016126871 A2 | 8/2016 |
| WO | WO-2016130578 A1 | 8/2016 |
| WO | WO-2017015075 A1 | 1/2017 |
| WO | WO-2017197343 A2 | 11/2017 |
| WO | WO-2018039338 A1 | 3/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2020041148 A1 | 2/2020 |

OTHER PUBLICATIONS

Aitman, et al. Copy number polymorphism in Fcgr3 predisposes to glomerulonephritis in rats and humans. Nature. Feb. 16, 2006;439(7078):851-5.

Akselband, "Enrichment of slow-growing marine microorganisms from mixed cultures using gel microdrop (GMD) growth assay and fluorescence-activated cell sorting", J. Exp. Marine Bioi., 329: 196-205 (2006).

Akselband, "Rapid mycobacteria drug susceptibility testing using gel microdrop (GMD) growth assay and flow cytometry", J. Microbiol. Methods, 62:181-197 (2005).

Anna, S.L., et al., "Formation of dispersions using "flow focusing" in microchannels," Applied Physics Letters, vol. 82, No. 3, pp. 364-366 (2003).

Attia, et al. Micro-injection moulding of polymer microfluidic devices. Microfluidics and nanofluidics. 2009; 7(1):1-28.

Zong, et al. Genome-wide detection of single-nucleotide and copy-number variations of a single human cell. Science. Dec. 21, 2012;338(6114):1622-6. doi: 10.1126/science.1229164.

Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.

Bansal et al. An MCMC algorithm for haplotype assembly from whole-genome sequence data,â€ (2008) Genome Res 18:1336-1346.

Bansal et al. "HapCUT: an efficient and accurate algorithm for the haplotype assembly problem," Bioinformatics (2008) 24:i153-i159

(56) References Cited

OTHER PUBLICATIONS

Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Bedtools: General Usage,â€ http://bedtools.readthedocs.io/en/latest/content/generalusage.html; Retrieved from the Internet Jul. 8, 2016.
Bentley et al. "Accurate whole human genome sequencing using reversible terminator chemistry," (2008) Nature 456:53-59.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Bray, "The JavaScript Object Notation (JSON) Data Interchange Format," Mar. 2014, retrieved from the Internet Feb. 15, 2015; https://tools.ietf.org/html/rfc715.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Zhao, J., et al., "Preparation of hemoglobin-loaded Nano-sized particles with porous structure as oxygen carriers," Biomaterials, vol. 28, pp. 1414-1422 (2007).
Browning, S.R. et al. "Haplotype Phasing: Existing Methods and New Developments" NaRevGenet (Sep. 16, 2011) 12(10):703-714.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Chaudhary "A rapid method of cloning functioNal variable-region antibody genese in *Escherichia coli* as single-chain imrnunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;l8(1):83-101.
Chen et al. BreakDancer: an algorithm for high-resolution mapping of genomic structural variation,â€ Nature Methods (2009) 6(9):677-681.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021/bm800867n. Epub Oct. 9, 2008.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-7-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Bioi. 15:427-437 (2008).
Cleary et al. Joint variant and de novo mutation identification on pedigrees from highthroughput sequencing data,â€ J Comput Biol (2014) 21:405-419.
Cook, et al. Copy-number variations associated with neuropsychiatric conditions. Nature. Oct. 16, 2008;455(7215):919-23. doi: 10.1038/nature07458.
De Bruin et al., UBS Investment Research. Q-Series®: DNa Sequencing. UBS Securities LLC. Jul. 12, 2007. 15 pages.
Demirci, et al. Single cell epitaxy by acoustic picolitre droplets. Lab Chip. Sep. 2007;7(9):1139-45. Epub Jul. 10, 2007.
Doerr, "The smallest bioreactor", Nature Methods, 2:5 326 (2005).
Dowding, et al. Oil core/polymer shell microcapsules by interNal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
"Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013."
Eid et al. Real-time sequencing form single polymerase molecules,â€ Science (2009) 323:133-138.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, "A micro fabricated fluorescence-activated cell sorter", Nature Biotech., 17:1109-1111 (1997).
Fulton et al., Advanced multiplexed analysis with the FlowMetrix system. Clin Chern. Sep. 1997;43(9): 1749-56.
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy, et al. Directed evolution of polymerase function by compartmentalized self-replication. Proc Natl Acad Sci U S A. Apr. 10, 2001;98(8):4552-7. Epub Mar. 27, 2001.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Gordon et al. Consed: A Graphical Tool for Sequence Finishing,â€ Genome Research (1998) 8:198-202.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Guo, et al. Droplet microfluidics for high-throughput biological assays. Lab Chip. Jun. 21, 2012;12(12):2146-55. doi: 10.1039/c2lc21147e. Epub Feb. 9, 2012.

(56) References Cited

OTHER PUBLICATIONS

Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNa-Seq by Multiplexed Linear Amplification. Cell Rep. Sep. 27, 2012;2(3):666-73. doi: 10.1016/j.celrep.2012.08.003. Epub Aug. 30, 2012.
He "Selective Encapsulation of Single Cells and Subcellular Organelles into Picoliter- and Femtoliter-Volume Droplets" ANal. Chern 77: 1539-1544 (2005).
Heng et al. "Fast and accurate long-read alignment with Burrows-Wheeler transform," Bioinformatics (2010) 25(14): 1754-1760.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Huang et al. EagleView: A genome assembly viewer for next-generationsequencing technologies,â€ Genome Research (2008) 18:1538-1543.
Huebner, "Quantitative detection of protein expression in single cells using droplet microfluidics", Chern. Commun. 1218-1220 (2007).
Hug, et al. Measurement of the number of molecules of a single mRNA species in a complex mRNA preparation. J Theor Biol. Apr. 21, 2003;221(4):615-24.
Illumina, Inc. An Introduction to Next-Generation Sequencing Technology. Feb. 28, 2012.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Jung, et al. Micro machining of injection mold inserts for fluidic channel of polymeric biochips. Sensors. 2007; 7(8):1643-1654.
Kanehisa et al. KEGG: Kyoto Encyclopedia of Genes and Genomes,â€ Nucleic Acids Research (2000) 28:27-30.
Khomiakov A et al., [Analysis of perfect and mismatched DNA duplexes by a generic hexanucleotide microchip]. Mol Bioi (Mosk). Jul.-Aug. 2003;37(4):726-41. Russian. Abstract only.
Kim et al., Albumin loaded microsphere of amphiphilic poly( ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functioNal microgels in microfluidic devices. Angew Chem Int Ed Engl. 2007;46(11):1819-22.
Kim et al. "HapEdit: an accuracy assessment viewer for haplotype assembly using massively parallel DNA-sequencing technologies," Nucleic Acids Research (2011) pp. 1-5.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. Sequencing of isolated sperm cells for direct haplotyping of a human genome,â€ Genome Res (2013) 23:826-832.
Kitzman et al. Haplotype-resolved genome sequencing of a Gujarati Indian individual.â€ Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Klein, et al. Droplet barcoding for single-cell transcriptomics applied to embryonic stem cells. Cell. May 21, 2015;161(5):1187-201. doi: 10.1016/j.cell.2015.04.044.
Knight, et al. Subtle chromosomal rearrangements in children with unexplained mental retardation. Lancet. Nov. 13, 1999;354(9191):1676-81.
Koster et al., "Drop-based microfluidic devices for encapsulation of single cells", Lab on a Chip The Royal Soc. of Chern. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagus, et al. A review of the theory, methods and recent applications of high-throughput single-cell droplet microfluidics. J. Phys. D: Appl. Phys. (2013) 46:114005. (21 pages).
Layer et al. LUMPY: A probabilistic framework for structural variant discovery,â€ Genome Biology (2014) 15(6):R84.
Li, Y., et al., "PEGylated PLGA Nanoparticles as protein carriers: synthesis, preparation and biodistribution in rats," JourNal of Controlled Release, vol. 71, pp. 203-211 (2001).
Lippert et al. Algorithmic strategies for the single nucleotide polymorphism haplotype assembly problem,â€ Brief. Bionform (2002) 3:23-31.
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Marcus. Gene method offers diagnostic hope. The Wall Street JourNal. Jul. 11, 2012.
Margulies et al. Genome sequencing in microfabricated high-density picoliter reactors,â€ Nature (2005) 437:376-380.
Zimmermann et at., Microscale production of hybridomas by hypo-osmolar electrofusion. Hum• Antibodies Hybridomas. Jan. 1992;3 (1 ): 14-8.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
McKenna et al. The Genome Analysis Toolkit: A MapReduce framework for anaylzing nextgeneration.
Merriman, et al. Progress in ion torrent semiconductor chip based sequencing. Electrophoresis. Dec. 2012;33(23):3397-417. doi: 10.1002/elps.201200424.
Microfluidic ChipShop. Microfluidic product catalogue. Mar. 2005.
Microfluidic ChipShop. Microfluidic product catalogue. Oct. 2009.
Miller et al. "Assembly Algorithms for next-generation sequencing data," Genomics, 95 (2010), pp. 315-327.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Mouritzen et al., Single nucleotide polymorphism genotyping using locked nucleic acid (LNa). Expert Rev Mol Diagn. Jan. 2003;3(1):27-38.
Myllykangas et al. "Efficient targeted resequencing of human germline and cancer genomes by oligonucleotide-selective sequencing," Nat Biotechnol, (2011) 29:1024-1027.
Nagashima, et al. Preparation of monodisperse poly (acrylamide-co-acrylic acid) hydrogel microspheres by a membrane emulsifica-

(56) References Cited

OTHER PUBLICATIONS tion technique and their size-dependent surface properties. Colloids and Surfaces B: Biointerfaces. Jun. 15, 1998; 11(1-2), 47-56.
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production ofMonodisperse Double Emulsions by Two-Step Droplet Breakup in Microfluidic Devices," Langmuir, vol. 20, pp. 9905-9908 (2004).
Perez, C., et al., "Poly(lactic acid)-poly(ethylene glycol) Nanoparticles as new carriers for the delivery ofplasmid DNa," JourNal of Controlled Release, vol. 75, pp. 211-224 (2001).
Peters, et al. Accurate whole-genome sequencing and haplotyping from 10 to 20 human cells. Nature. Jul. 11, 2012;487(7406):190-5. doi: 10.1038/Nature11236.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Pushkarev et al. Single-molecule sequencing of an individual human genome,â€ Nature Biotech (2009) 17:847-850.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Ryan, "Rapid assay for mycobacterial growth and antibiotic susceptibility using gel microdrop and encapsulation", J. Clinical Microbial., 33:7 1720-1726 (1995).
Schirinzi et al., Combinatorial sequencing-by-hybridization: aNalysis of the NFI gene. Genet Test. 2006 Spring;10(1):8-17.
Schmitt, "Bead-based multiplex genotyping of human papillomaviruses", J. Clinical Microbial., 44:2 504-512 (2006).
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shah, "Fabrication of mono disperse thermosensitive microgels and gel capsules in micro fluidic devices", Soft Matter, 4:2303-2309 (2008).
Shendure et al. Accurate Multiplex Polony Sequencing of an Evolved bacterial Genomeâ€ Science (2005) 309:1728-1732.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci USA. Aug. 12, 2008;105(32):11264-9. doi: 10.1073/pnas.0802970105. Epub Aug. 6, 2008.
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., DiscrimiNation between perfect and mismatched duplexes with oligonucleotide gel microchips: role of thermodyNamic and kinetic effects during hybridization. J Biomol Struct Dyn. Jun. 2005;22(6):725-34.
SSH Tunnel—Local and Remote Port Forwarding Explained With Examples,â€ Trackets Blog, http://blog.trackets.com/2014/05/17/ssh-tunnel-local-and-remote-port-forwarding-explained-with-examples.html; Retrieved from the Internet Jul. 7, 2016.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese JourNal Experimental Surgery. May 2005;22(5):639-40.
Tawfik, D.S., et al., "Man-made cell-like compartments for molecular evolution," Nature Biotechnology, vol. 16, pp. 652-656 (1998).
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Tewhey et al. The importance of phase information for human genomics,â€ Nat Rev Genet (2011) 12:215-223.
The SAM/BAM Format Specificatio Working Group, "Sequence Allignment/ Map Format Specification," Dec. 28, 2014.
Theberge, et al. Microdropelts in microfluidics: an evolving platform for discoveries in chemsitry and biology. Angew Chem Int Ed Engl. Aug. 9, 2010;49(34):5846-68. doi: 10.1002/anie.200906653.
Tonelli, et al. Perfluoropolyether functional oligomers: unusual reactivity in organic chemistry. Journal of fluorine chemistry. 2002; 118(1)"107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Methods for genomic partitioning. Annu Rev Genomics Hum Genet. 2009;10:263-84. doi: 10.1146/annurev-genom-082908-150112. Review.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., Single nucleotide polymorphism discrimiNation assisted by improved base stacking hybridization using oligonucleotide microarrays. Biotechniques. 2003;35:300-08.
Weaver, "Rapid clonal growth measurements at the single-cell level: gel microdroplets and flow cytometry", Biotechnology, 9:873-877 (1991).
Wheeler et al., "Database resources of the National Center for Biotechnology Information," Nucleic Acids Res. (2007) 35 (Database issue): D5-12.
Whitesides, "Soft lithography in biology and biochemistry", Annual Review of Biomedical Engineering, 3:335-373 (2001).
Williams et al., Amplification of complex gene libraries by emulsion PCR, Nature Methods 3(7):545-550 (2006).
Woo, et al. G/C-modified oligodeoxynucleotides with selective complementarity: synthesis and hybridization properties. Nucleic Acids Res. Jul. 1, 1996;24(13):2470-5.
Xia and Whitesides, Soft Lithography, Ann. Rev. Mat. Sci. 28:153-184 (1998).
Yamamoto, et al. Chemical modification of Ce(IV)/EDTA-base artificial restriction DNa cutter for versatile manipulation of doulbe-stranded DNa. Nucleic Acids Research. 2007; 35(7):e53.

(56) References Cited

OTHER PUBLICATIONS

Zerbino, Daniel, "Velvet Manual—version 1.1," Aug. 15, 2008, pp. 1-22.
Zerbino et al. "Velvet: Algorithms for de novo short read assembly using de Bruijn graphs," Genome Research (2008) 18:821-829.
Zhang, "Combinatorial marking of cells and organelles with reconstituted fluorescent proteins", Cell, 119:137-144 (Oct. 1, 2004).
Co-pending U.S. Appl. No. 15/985,388, filed May 21, 2018.
Margulies 2005 Supplementary methods (Year: 2005).
Lo, et al. On the design of clone-based haplotyping. Genome Biol. 2013;14(9):R100.
Jarosz, M. et al. "Using 1 ng of DNA to detect haplotype phasing and gene fusions from whole exome sequencing of cancer cell lines" Cancer Res (2015) 75(suppl5):4742.
McCoy, R. et al. "Illumina TruSeq Synthetic Long-Reads Empower De Novo Assembly and Resolve Complex, Highly-Repetitive Transposable Elements" Plos (2014) 9(9):e1016689.
Ritz, A. et al. "Characterization of structural variants with single molecule and hybrid sequencing approaches" Bioinformatics (2014) 30(24):3458-3466.
Ekblom, R. et al. "A field guide to whole-genome sequencing, assembly and annotation" Evolutionary Apps (Jun. 24, 2014) 7(9):1026-1042.
Voskoboynik, A. et al. The genome sequence of the colonial chordate, Botryllus schlosseri. eLife, 2:e00569 (2013). doi: 10.7554/eLife.00569. Epub Jul. 2, 2013.
Zerbino, D.R. "Using the Velvet de novo assembler for short-read sequencing technologies" Curr Protoc Bioinformatics. Sep. 2010;Chapter 11:Unit 11.5. doi: 10.1002/0471250953.bi1105s31.
Co-pending U.S. Appl. No. 15/730,119, filed Oct. 11, 2017.
Zheng, X.Y. et al. "Haplotyping germline and cancer genomes with high-throughput linked-read sequencing" Nature Biotech (Feb. 1, 2016) 34(3):303-311.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Adamson et al., "Production of arrays of chemically distinct nanolitre plugs via repeated splitting in microfluidic devices", Lab Chip 6(9):1178-1186 (Sep. 2006).
Agasti, S.S. et al. "Photocleavable DNA barcode-antibody conjugates allow sensitive and multiplexed protein analysis in single cell" J Am Chem Soc (2012) 134(45):18499-18502.
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Brenner, et al. "In vitro cloning of complex mixtures of DNA on microbeads: physical separation of differentially expressed cDNAs." Proc Natl Acad Sci U S A. Feb. 15, 2000;97(4):1665-70.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Chien et al. "Multiport flow-control system for lab-on-a-chip microfluidic devices", Fresenius J. Anal Chem, 371:106-111 (Jul. 27, 2001).
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,102, filed Jun. 6, 2019.
Co-pending U.S. Appl. No. 16/530,930, filed Aug. 2, 2019.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Depristo et al. A framework for variation discovery and genotyping using next-generation DNA sequencing data. Nature Genet 43:491-498 (2011).
Duffy et al., Rapid Protyping of Microfluidic Systems and Polydimethylsiloxane, Anal Chem 70:4974-4984 (1998).
Gericke, et al. Functional cellulose beads: preparation, characterization, and applications. Chemical reviews 113.7 (2013): 4812-4836.
Hiatt, et al. Parallel, tag-directed assembly of locally derived short sequence reads. Nat Methods. Feb. 2010;7(2):119-22. Epub Jan. 17, 2010.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kivioja, et al. Counting absolute numbers of molecules using unique molecular identifiers. Nat Methods. Nov. 20, 2011;9(1):72-4.
Korlach et al., Methods in Enzymology, Real-Time DNA Sequencing from Single Polymerase Molecules, (2010) 472:431-455.
Lagally, et al. Single-Molecular DNA Amplification and Analysis in an Integrated Microfluidic Device. Anal Chem. Feb. 1, 2001;73(3):565-70.
Lennon et al. A scalable, fully automated process for construction of sequence-ready barcoded libraries for 454. Genome Biology 11:R15 (2010).
Madl, et al. "Bioorthogonal Strategies for Engineering Extracellular matrices", Madal, Chritopher, Adv. Funct. Master. Jan. 19, 2018, vol. 28, 1706046, pp. 1-21.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Orakdogen, N. "Novel responsive poly(N,N-dimethylaminoethyl methacrylate) gel beads: preparation, mechanical properties and pH-dependent swelling behavior" J Polym Res (2012) 19:9914.

(56) References Cited

OTHER PUBLICATIONS

Perrott, Jimmy. Optimization and Improvement of Emulsion PCR for the Ion Torrent Next-Generation Sequencing Platform. (2011) Thesis.

Priest, et al. Generation of Monodisperse Gel Emulsions in a Microfluidic Device, Applied Physics Letters, 88:024106 (2006).

Ramsey, J.M. "The burgeoning power of the shrinking laboratory" Nature Biotech (1999) 17:1061-1062.

Ramskold et al. (2012) "Full-length mRNA-Seq from single-cell levels of RNA and individual circulating tumor cells" Nature Biotechnology 30(8):777-782.

Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 Using MultiplexIdentifierAdaptorsForTheGSFLXTitaniumSeriesChemistry-BasicMIDSet.pdf.

Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.

Schubert, et al. Microemulsifying fluorinated oils with mixtures of fluorinated and hydrogenated surfactants. Colloids and Surfaces A; Physicochemical and Engineering Aspects, 84(1994) 97-106.

Seiffert, et al. Microfluidic fabrication of smart microgels from macromolecular precursors.Polymer. vol. 51, Issue 25, Nov. 26, 2010, pp. 5883-5889.

Smith, et al. Highly-multiplexed barcode sequencing: an efficient method for parallel analysis of pooled samples. Nucleic Acids Research, 38(13): e142 (2010).

Song, et al. Reactions in droplets in microfluidic channels. Angew Chem Int Ed Engl. Nov. 13, 2006;45(44):7336-56.

Thaxton, C.S. et al. "A Bio-Bar-Code Assay Based Upon Dithiothreitol Oligonucleotide Release" Anal Chem (2005) 77:8174-8178.

Thorsen, et al. Dynamic pattern formation in a vesicle-generating microfluidic device. Physical Review Letters. American Physical Society. 2001; 86(18):4163-4166.

Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

Uttamapinant, et al. Fast, cell-compatible click chemistry with copper-chelating azides for biomolecular labeling.Angew. Chem. Int. End. Engl., Jun. 11, 2012: 51(24) pp. 5852-5856.

Weigl, et al. Microfluidic Diffusion-Based Separation and Detection. Science. 1999; pp. 346-347.

Zhang, et al. One-step fabrication of supramolecular microcapsules from microfluidic droplets. Science. Feb. 10, 2012;335(6069):690-4. doi: 10.1126/science.1215416.

Zhang, et al. Reconstruction of DNA sequencing by hybridization. Bioinformatics. Jan. 2003;19(1):14-21.

Zheng, et al. Massively parallel digital transcriptional profiling of single cells. Nat Commun. Jan. 16, 2017;8:14049. doi: 10.1038/ncomms14049.

Zheng, X. SeqArray: an R/Bioconductor Package for Big Data Management of Genome-Wide Sequencing Variants, Department of Biostatistics; University of Washington-Seattle; Dec. 28, 2014.

Zhu, et al. Reverse transcriptase template switching: a SMART approach for full-length cDNA library construction. Biotechniques. Apr. 2001;30(4):892-7.

[1] +4:102,079,023-102,085,763

SEQ ID NO: 1 AAAAAAAAAAAAAAAAAAAAAAAAAACCTCTCAGTCTTCATGACCAGTTTCAAAATAGTTCTATTTTTAATTCATGTCTAAAA
SEQ ID NO: 2 AAAAAAAAAAAAAAAAAAAAAAAAAACCTCTCAGTCTTCATGACCAGTTTCAAAATAGTTCTATTTTTAATTCATGTCTAAAA (4560 matching bases)

SEQ ID NO: 3 GCGACAGAGCAAGACTCCATCAAAATAAATAAATAAATAAATAAATAAATAAATAAATAAATAAATAAAGGGAAATGTAT
SEQ ID NO: 4 GCGACAGAGCAAGACTCCATCA     AAATAAATAAATAAATAAATAAATAAATAAATAAATAAAGGGAAATGTAT (1440 matching bases)

SEQ ID NO: 5 CAGGCTGGAGTGCAGTGGTGTAATCATAACTTACTGCATCTTTGAATTCCTGTGCCATCAACTGATCCTCGCACCTCAGC
SEQ ID NO: 6 CAGGCTGGAGTGCAGTGGTGTAATCATAACTTACTGCATCTTTGAATTCCTGTGCCATCAACTGATCCT

SEQ ID NO: 5 CTCCTGACCAGCTGGGATTACAGACATTCACCACAGAGCCTGGCTAATTTTTTTGTAGAGACAGGGTCTTACTTTGTTGC

SEQ ID NO: 5 CCAGGCTGGTCTCAAACTCCTAGCTTCAAGCGATCTGCCTGCCCTAGCCTCTCAAAGTGCTGGGATTACAAGTGTGAGCT

SEQ ID NO: 5 ACTGTGCCTGGCCACATGACAGAGTTCTAGTATCTGTAATTTCACATCCAGGCCTTCATTCTCTCCACCTATAAACGTCC

SEQ ID NO: 5 ACTGGAACACAATTGGAAGAAAATATTGGTAAAAACGTTGTTCCTTTCATGAGCAGCATAAGCAGTATGTTATATAATTT

SEQ ID NO: 5 AATCTAATTCAGCGTTAATAAATACTCAAGTTTAAATTTTACCAAAACAAACCCATTAATTACAAATGAAGTAACCCAAG

SEQ ID NO: 5 GTTTATAGGATGACAGACTCTTAGCAATACTATGAAAGAAACCACAATAAGGTATACTGCCTTCAGCCTGCTCACTCTGA

SEQ ID NO: 5 GTCACACTTGCCTCCTTGATGTTGTAATATTTCTTTCTGGGAGCCAAGCTCCAGCTGTTCACACTGTGAAGAGCCCTTCC
SEQ ID NO: 6                                                                CTGTGAAGAGCCCTTCC (400 matching bases)

SEQ ID NO: 7 AAGGTCCTATCAGTTCTGTATAACTTGCTATTTCTAAAAATAATGGGATTTAAGTTTTTTTTTTTTTTTTTAGGGTTCT
SEQ ID NO: 8 AAGGTCCTATCAGTTCTGTATAACTTGCTATTTCTAAAAATAATGGGATTTAAG   TTTTTTTTTTTTTTTAGGGTCCT (21 matching bases)

*FIG. 1*

| SEQ ID NO: | |
|---|---|
| 9 | 24446 CAAAAAAAAAAAAAAAAAAAAAAAAAAAAAAAAAAAAAAGAGGTATCTTTTGCTTGGCTCTTGTCCATATCTGCTG |
| 10 | match C AAAAAAAAAAAAAAAAAAAAAAAAAAAAAAAAAAAAAAGAGGTATCTTTTGCTTGGCTCTTGTCCATATCTGCTG |
| | |
| 11 | 32006 CACTCCAGCCTGGGCTGTCTCAAAAAAAAAAAAAAAAAAAAAAAAAAAAAAAAGGGAAGGAAGGAAGGAAGAGAGA |
| 12 | match CACTCCAGCCTGGGCTGTCTCAAAAAAAAAAAAAAAAAAAAAAAAAAAAAAAA GGAAGGAAGGAAGGAAGAGAGA |
| | |
| 13 | 4806 TACTACTCTGAGTCACATCTTTTTTTTTTTTTTTTTTTTTTTTTTTTTTTTTGAGACAGGGTCTCGCTCTGTCA |
| 14 | match TACTACTCTGAGTCACATC TTTTTTTTTTTTTTTTTTTTTTTTTTTTTTTGAGACAGGGTCTCGCTCTGTCA |
| | |
| 15 | 11920 TTTCTCATGTTATAATTTTCTTCCTTATTTTAAAGGGTTTACTTTATGGTTCATTTTTTTTTAACTTT 585 |
| 16 | match TTTCTCATGTTATAATTTTCTTCCTTATTTTAAAGGGTTTACTTTATGGTTCATTTTTTTTTAACTTT match |
| | |
| | [1765 missing bases] |
| | |
| 17 | 52166 CAACAGAGCAAAACTCTGTCTCAAAAAAAGCAAAAAACAACAACAACAAAAAAAAAA     AAAAA |
| 18 | match CAACAGAGCAAAACTCTGTCTCAAAAAAAGCAAAAAACAACAACAACAAAAAAAAAAAAAAAAAAAAAAAA |
| | |
| 17 | AAAAAAAACAAGAAGCAGCGCACCAGATTTAGCCCAGGGGGCGGTAGTTCACAAAGTCCAGATCAGTGTCGTCCCAGAGA |
| 18 | AAAAAAAACAAGAAGCAGCGCACCAGATTTAGCCCAGGGGGCGGTAGTTCACAAAGTCCAGATCAGTGTCGTCCCAGAGA |
| | |
| 19 | 11766 AGAGCAAGATTCCGAAAAAAAAAAAAAAAAAAAAAAAAAAAAACACCGTCAGGTCTCGTGAGAACTCACTCTCAC |
| 20 | match AGAGCAAGATTCCGAAAAAAAAAAAAAAAAAAAAAAAAAAAAA CACCGTCAGGTCTCGTGAGAACTCACTCTCAC |
| | |
| 21 | 15258 GGGCAACAGAGCAAGACTCCATCTCAAAAAAAAAAAAAAAAAAAGGAGTTCCCCTGCACAAGCTCTCTC 5592 |
| 22 | match GGGCAACAGAGCAAGACTCCATCTCAAAAAAAAAAAAAAAAAAA GGAGTTCCCCTGCACAAGCTCTCTC match |
| | |
| | [46 missing bases] |
| | |
| 23 | AGAAAGAAAGAAAGAAAGAAAGAAAGAAAGAAAGAAAGAAAGAGAAAGAAAGAGAGAGAGAGAAAGAGAGAGAA 1373 |
| 24 | AGAAAGAAAGAAAGAAAGAAAGAAAGAAAGAAAGAAAGAAAGAGAAAGAAAGAGAGAGAGAGAAAGAGAGAGAA match |

*FIG. 8*

SEQUENCE LISTING

```
<160> NUMBER OF SEQ ID NOS: 24

<210> SEQ ID NO 1
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaaaaaa aaaaaaaaaa aaacctctca gtcttcatga ccagtttcaa aatagttcta        60
tttttaattc atgtctaaaa                                                    80

<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaaaaaaa aaaaaaaaaa aaacctctca gtcttcatga ccagtttcaa aatagttcta        60
tttttaattc atgtctaaaa                                                    80

<210> SEQ ID NO 3
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcgacagagc aagactccat caaaataaat aaataaataa ataaataaat aaataaataa        60
ataaataaag ggaaatgtat                                                    80
```

<210> SEQ ID NO 4
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4

```
gcgacagagc aagactccat caaaataaat aaataaataa ataaataaat aaataaataa    60
ataaagggaa atgtat                                                    76
```

<210> SEQ ID NO 5
<211> LENGTH: 640
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
caggctggag tgcagtggtg taatcataac ttactgcatc tttgaattcc tgtgccatca    60
actgatcctc gcacctcagc ctcctgacca gctgggatta cagacattca ccacagagcc   120
tggctaattt ttttgtagag acagggtctt actttgttgc ccaggctggt ctcaaactcc   180
tagcttcaag cgatctgcct gccctagcct ctcaaagtgc tgggattaca agtgtgagct   240
actgtgcctg gccacatgac agagttctag tatctgtaat ttcacatcca ggccttcatt   300
ctctccacct ataaacgtcc actggaacac aattggaaga aaatattggt aaaaacgttg   360
ttcctttcat gagcagcata agcagtatgt tatataattt aatctaattc agcgttaata   420
aatactcaag tttaaatttt accaaaacaa acccattaat tacaaatgaa gtaacccaag   480
gtttatagga tgacagactc ttagcaatac tatgaaagaa accacaataa ggtatactgc   540
cttcagcctg ctcactctga gtcacacttg cctccttgat gttgtaatat ttctttctgg   600
gagccaagct ccagctgttc acactgtgaa gagcccttcc                         640
```

<210> SEQ ID NO 6
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6

```
caggctggag tgcagtggtg taatcataac ttactgcatc tttgaattcc tgtgccatca    60
actgatcctc tgtgaagagc ccttcc                                         86
```

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7

```
aaggtcctat cagttctgta taacttgcta tttctaaaaa taatgggatt taagtttttt    60
tttttttttt ttagggttct                                                80
```

```
<210> SEQ ID NO 8
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaggtcctat cagttctgta taacttgcta tttctaaaaa taatgggatt taagtttttt    60
ttttttttta gggtcct                                                   77

<210> SEQ ID NO 9
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caaaaaaaaa aaaaaaaaaa aaaaaaaaaa aaaaaaagag gtatcttttg cttggctctt    60
gtccatatct gctg                                                      74

<210> SEQ ID NO 10
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caaaaaaaaa aaaaaaaaaa aaaaaaaaaa aaaaagaggt atcttttgct tggctcttgt    60
ccatatctgc tg                                                        72

<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cactccagcc tgggctgtct caaaaaaaaa aaaaaaaaaa aaaaaaaaaa agggaaggaa    60
ggaaggaaga gaga                                                      74

<210> SEQ ID NO 12
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cactccagcc tgggctgtct caaaaaaaaa aaaaaaaaaa aaaaaaaaaa ggaaggaagg    60
aaggaagaga ga                                                        72

<210> SEQ ID NO 13
<211> LENGTH: 74
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 13
tactactctg agtcacatct tttttttttt tttttttttt tttttttttt ttgagacagg      60
gtctcgctct gtca                                                       74

<210> SEQ ID NO 14
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tactactctg agtcacatct tttttttttt tttttttttt tttttttttt gagacagggt      60
ctcgctctgt ca                                                         72

<210> SEQ ID NO 15
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tttctcatgt tataattttc ttccttattt taaagggttt actttatggt tcattttttt      60
ttaacttt                                                              68

<210> SEQ ID NO 16
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tttctcatgt tataattttc ctccttattt taaagggttt actttatggt tcattttttt      60
ttaacttt                                                              68

<210> SEQ ID NO 17
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
caacagagca aaactctgtc tcaaaaaagc aaaaaacaac aacaacaaca aaaaaaaaaa      60
aaaaaaaaaa acaagaagca gcgcaccaga tttagcccag ggggcggtag ttcacaaagt     120
ccagatcagt gtcgtcccag aga                                            143

<210> SEQ ID NO 18
<211> LENGTH: 154
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18
caacagagca aaactctgtc tcaaaaaagc aaaaacaac aacaacaaca aaaaaaaaa    60 aaaaaaaaaa aaaaaaaaaa aacaagaagc agcgcaccag atttagccca gggggcggta   120
gttcacaaag tccagatcag tgtcgtccca gaga                              154

<210> SEQ ID NO 19
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agagcaagat tccgaaaaaa aaaaaaaaa aaaaaaaaa aacaccgtca ggtctcgtga     60
gaactcactc tcac                                                    74

<210> SEQ ID NO 20
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agagcaagat tccgaaaaaa aaaaaaaaa aaaaaaaaa acaccgtcag gtctcgtgag     60
aactcactct cac                                                     73

<210> SEQ ID NO 21
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gggcaacaga gcaagactcc atctcaaaaa aaaaaaaaa aaaggagttc ccctgcacaa    60
gctctctc                                                           68

<210> SEQ ID NO 22
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gggcaacaga gcaagactcc atctcaaaaa aaaaaaaaa aaggagttcc cctgcacaag    60
ctctctc                                                            67

<210> SEQ ID NO 23
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

```
-continued

<400> SEQUENCE: 23
agaaagaaag aaagaaagaa agaaagaaag aaagaaagaa agagaaagaa agagagagag        60
agaaagagag agaa                                                         74

<210> SEQ ID NO 24
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agaaagaaag aaagaaagaa agaaagaaag aaagaaagaa agagaaagaa agagagagag        60
agaaagagag agaa                                                         74
```

SYSTEMS, METHODS, AND MEDIA FOR DE NOVO ASSEMBLY OF WHOLE GENOME SEQUENCE DATA

CROSS REFERENCE

This application claims the benefit of U.S. Application Ser. No. 62/294,184, filed Feb. 11, 2016, and U.S. Application Ser. No. 62/332,914 filed May 6, 2016, both of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Nov. 16, 2016, is named 43487-741_201_SL.txt and is 8,711 bytes in size.

BACKGROUND OF THE INVENTION

Genomic sequencing holds great promise for the fields of medicine, forensics and biotechnology. A variety of DNA sequencing methods have been developed based on different sequencing chemistries and machines that carry out genomic sequencing have grown more robust and efficient. Technologically, the speed at which raw genomic data can be acquired exceeds the ability to assemble this raw data into a genome—especially diploid or polyploid genomes. Current sequence assembly methods are complicated, require a large amount of processor capability, and take up large amounts of memory.

SUMMARY OF THE INVENTION

Determining the genome sequence of an individual living organism or tissue is of fundamental importance to biology and medicine. Decades of research have yielded a vast array of laboratory and computational approaches directed at this problem. These vary dramatically in their aggregate experimental burden, including input DNA amount, cost, complexity, and timeline, with greater burden tending to yield a higher quality genome sequence.

At the low end, some methods sequence short fragments of DNA, then align the resulting reads to a haploid reference sequence from the same species, to identify differences with it, thereby partially inferring the sequence of the sample. The methods have been used to generate and analyze over a thousand human samples each, yielding extraordinarily deep information across populations. However, these methods may be intrinsically biased by the reference comparison and in general cannot identify sequences that are novel to the given sample or which represent large-scale changes, nor can they distinguish between changes on parental alleles.

By contrast, data (often from long DNA fragments) may be synthesized in the process known as de novo assembly, without exploiting a reference sequence, and which is particularly difficult for large and complex genomes. A core challenge is the correct representation of highly similar sequences. A particularly formidable instance appears in eukaryotes, wherein sexual reproduction contributes maternal and paternal chromosome "copies." While these copies will be quite similar for long stretches, some regions can differ dramatically, leading not only to small scale differences but often to gene copy number differences. As homologous chromosomes encode separate gene copies, knowledge of their separate sequences is required to understand phenotype.

Yet even for high-end de novo laboratory formulations, the standard of the field has been to computationally weave homologous chromosomes, yielding, for each locus, a single haploid consensus that is generally not present in nature. Better, one would generate a haploid assembly together with a phased catalog of differences between the two originating chromosomes.

The disclosure provided herein bridges the gap between low- and high-end approaches, by creating true diploid, de novo assemblies, at very low experimental burden. The disclosed technology is also based on genome partitioning, using an automated microfluidic system. The technology is able to generate the entirety of data for an assembly project from one library. Moreover, the disclosed methodology starts from about one nanogram of high molecular weight DNA, about a million times less than alternative approaches. Advantageously, the cost of the data is in the range of low-end methods based on read alignment and no expertise is required for assembly, because the process is automatic.

The present disclosure provides platforms, systems, media, and methods for the de novo assembly of whole-genome sequencing reads into a complete genome using short DNA sequence reads. The methods are compatible with any short-read sequencing technology. The methods described herein are advantageously deployed to "phase" contigs into larger sequence blocks and resolve genomic structural variation such as large indels, duplications, and translocations.

The methods of the disclosure possess many advantages compared to other short-read assembly techniques and long-read techniques, such as single molecule real-time (SMRT) sequencing. Some of the advantages include: reductions in input DNA, reduced requirements for sequence coverage, reduced assembly time, reduced processing requirements, commercial scalability due to the ability to run on commoditized computer resources, and an overall increase in efficiency and cost effectiveness. For example, the methods of this disclosure allow for a nearly 180-fold reduction in processing power and a 21-fold reduction in memory utilization, compared to the FALCON assembler from Pacific Biosciences (PacBio), which utilizes SMRT technology.

Additionally, long-read sequencing technologies are limited by the average read length of the technology such as 10-20 kb. The technology described herein has been shown to generate fully phased contigs ranging from 85-105 kb and fully phased sequence blocks at least 5 Mb in length.

In one aspect, disclosed herein is a computer-implemented method of de novo genome assembly for nucleic acid sequence data generated from a nucleic acid sample of an organism, the method comprising: generating, by one or more computers, an initial assembly based on short-read sequence data, the initial assembly comprising one or more areas of unresolved sequence ambiguity, wherein the short-read sequence data is derived from longer starting sequences from the nucleic acid sequence data and is tagged to preserve long-range sequence context for the organism such that a subset of the short-read sequence data derived from a common starting sequence share a common tag; generating, by the one or more computers, a plurality of local assemblies based on the initial assembly by utilizing the tags to resolve a plurality of areas of sequence ambiguity; generating, by the one or more computers, a global assembly based on the plurality of local assemblies; cleaning, by the one or more computers, the global assembly by removing sequence data inconsistent with the long-range sequence context indicated by the tags; and generating, by the one or more computers, a phased genome assembly based on the global assembly by utilizing the tags to separate phased nucleotide sequence; wherein the phased genome assembly is achieved without alignment to a reference sequence or any independently generated genome sequence. In certain instances, the genome is diploid. In certain instances, the short-read sequence data is generated from a single sequencing library. In certain instances, the short-read sequence data results in 50× or less coverage of the genome of the organism. In certain instances, the short-read sequence data is tagged to preserve context over a starting sequence 2×-1000× longer than the reads. In certain instances, the short-read sequence data is tagged to preserve context over a starting sequence of 10 kb-5 Mb. The initial assembly can be an initial assembly graph. In certain embodiments, the initial assembly graph is generated by: identifying a plurality of k-mers that have a high probability of being present in the genome of the organism; using the tags to filter the plurality of k-mers based on the number of starting sequences each k-mer occurs in; and bringing together k-mers in the plurality of k-mers sharing a common 1-mer to form an initial assembly, wherein 1<k. The method can further comprise revising, by the one or more computers, the initial assembly graph by: eliminating one or more areas of sequence ambiguity based on a number of reads available for each option within an area of sequence ambiguity; and filling in gaps in the initial assembly graph by consulting the original short-read sequence data. K can be between 24 and 96. The plurality of local assemblies can be generated by: using the initial assembly graph as in interim reference; identifying edges of unambiguous sequence; identifying neighboring edges sharing a number of tags above a threshold number of tags; and bringing together edges of unambiguous sequence with the identified neighboring edges. The global assembly can be generated by: identifying a plurality of z-mers in the plurality of local assemblies that have a high probability of being present in the genome of the organism, wherein z>k; and bringing together the z-mers in the plurality of local assemblies. Z can be between 100 and 300. The short-read sequence data can be generated from less than 10 ng of DNA input material. The short-read sequence data can be generated from less than 2 ng of DNA input material. In some embodiments, the assembly can be completed in less than 60 minutes. In these embodiments, the one or more computers can comprise less than 512 GB of storage; in certain embodiments the one or more computers can comprise less than 60 GB of storage. In certain instances, the assembly is completed in less than 20 minutes. In these instances, the one or more computers comprise less than 512 GB of storage. In certain instances, the one or more computers comprise less than 60 GB of storage. In certain instances, the organism is a human being. In certain instances, the DNA sequence data is whole genome sequence data and the phased genome assembly is a whole genome assembly. In certain instances, the one or more computers occupy one cubic foot or less of physical space.

In another aspect, disclosed herein is a computer-implemented system comprising: a digital processing device comprising: at least one processor, an operating system configured to perform executable instructions, a memory, and a computer program including instructions executable by the digital processing device to create a de novo genome assembly application for nucleic acid sequence data generated from a nucleic acid sample of an organism, the application comprising: a first software module generating an initial assembly based on short-read sequence data, the initial assembly comprising one or more areas of unresolved sequence ambiguity, wherein the short-read sequence data is derived from longer starting sequences from the nucleic acid sequence data and is tagged to preserve long-range sequence context for the organism such that a subset of the short-read sequence data derived from a common starting sequence share a common tag; a second software module generating a plurality of local assemblies based on the initial assembly by utilizing the tags to resolve a plurality of areas of sequence ambiguity; a third software module generating a global assembly based on the plurality of local assemblies; a fourth software module cleaning the global assembly by removing sequence data inconsistent with the long-range sequence context indicated by the tags; and a fifth software module generating a phased genome assembly based on the global assembly by utilizing the tags to separate homologous phased nucleotide sequence; wherein the phased genome assembly is achieved without alignment to a reference sequence or any independently generated genome sequence In certain instances, the genome is diploid. In certain instances, the short-read sequence data is generated from a single sequencing library. In certain instances, the short-read sequence data results in 50× or less coverage of the genome of the organism. In certain instances, the short-read sequence data is tagged to preserve context over a starting sequence 2×-1000× longer than the reads. In certain instances, the short-read sequence data is tagged to preserve context over a starting sequence of 10 kb-5 Mb. In certain instances, the initial assembly is an initial assembly graph. In certain instances the software module generates an initial assembly graph generates the initial assembly graph by identifying a plurality of k-mers that have a high probability of being present in the genome of the organism; using the tags to filter the plurality of k-mers based on the number of starting sequences each k-mer occurs in; and bringing together k-mers in the plurality of k-mers sharing a common 1-mer to form an initial assembly, wherein 1<k. In certain instances, the software module generates an initial assembly graph revises the initial assembly graph by: eliminating one or more areas of sequence ambiguity based on a number of reads available for each option within an area of sequence ambiguity; and filling in gaps in the initial assembly graph by consulting the original short-read sequence data. K can be between 24 and 96. The plurality of local assemblies can be generated by: using the initial assembly graph as in interim reference; identifying edges of unambiguous sequence; identifying neighboring edges sharing a number of tags above a threshold number of tags; and bringing together edges of unambiguous sequence with the identified neighboring edges. The global assembly can be generated by: identifying a plurality of z-mers in the plurality of local assemblies that have a high probability of being present in the genome of the organism, wherein z>k; and bringing together the z-mers in the plurality of local assemblies. Z can be between 100 and 300. The short-read sequence data can be generated from less than 10 ng of DNA input material. The short-read sequence data can be generated from less than 2 ng of DNA input material. In certain instances, the assembly is completed in less than 60 minutes. In some embodiments, the assembly can be completed in less than 60 minutes. In these embodiments, the one or more computers can comprise less than 512 GB of storage; in certain embodiments the one or more computers can comprise less than 60 GB of storage. In certain instances, the assembly is completed in less than 20 minutes. In these instances, the one or more computers comprise less than 512 GB of storage. In certain instances, the one or more computers comprise less than 60 GB of storage. In certain instances, the organism is a human being. In certain instances, the DNA sequence data is whole genome sequence data and the phased genome assembly is a whole genome assembly. In certain instances, the digital processing device occupies one cubic foot or less of physical space.

In another aspect, disclosed herein is a non-transitory computer-readable storage media encoded with a computer program including instructions executable by a processing device to create a de novo genome assembly application for nucleic acid sequence data generated from a nucleic acid sample of an organism, the application comprising: a first software module generating an initial assembly based on short-read sequence data, the initial assembly comprising one or more areas of unresolved sequence ambiguity, wherein the short-read sequence data is derived from longer starting sequences from the nucleic acid sequence data and is tagged to preserve long-range sequence context for the organism such that a subset of the short-read sequence data derived from a common starting sequence share a common tag; a second software module generating a plurality of local assemblies based on the initial assembly by utilizing the tags to resolve a plurality of areas of sequence ambiguity; a third software module generating a global assembly based on the plurality of local assemblies; a fourth software module cleaning the global assembly by removing sequence data inconsistent with the long-range sequence context indicated by the tags; and a fifth software module generating a phased genome assembly based on the global assembly by utilizing the tags to separate homologous phased nucleotide sequence; wherein the phased genome assembly is achieved without alignment to a reference sequence or any independently generated genome sequence. In certain instances, the genome is diploid. In certain instances, the short-read sequence data is generated from a single sequencing library. In certain instances, the short-read sequence data results in 50× or less coverage of the genome of the organism. In certain instances, the short-read sequence data is tagged to preserve context over a starting sequence 2×-1000× longer than the reads. In certain instances, the short-read sequence data is tagged to preserve context over a starting sequence of 10 kb-5 Mb. In certain instances, the initial assembly is an initial assembly graph. In certain instances, the software module generating an initial assembly graph generates the initial assembly graph by: identifying a plurality of k-mers that have a high probability of being present in the genome of the organism; using the tags to filter the plurality of k-mers based on the number of starting sequences each k-mer occurs in; and bringing together k-mers in the plurality of k-mers sharing a common 1-mer to form an initial assembly, wherein 1<k. In certain instances, the software module generating an initial assembly graph revises the initial assembly graph by: eliminating one or more areas of sequence ambiguity based on a number of reads available for each option within an area of sequence ambiguity; and filling in gaps in the initial assembly graph by consulting the original short-read sequence data. K can be between 24 and 96. The plurality of local assemblies can be generated by: using the initial assembly graph as in interim reference; identifying edges of unambiguous sequence; identifying neighboring edges sharing a number of tags above a threshold number of tags; and bringing together edges of unambiguous sequence with the identified neighboring edges. The global assembly can be generated by: identifying a plurality of z-mers in the plurality of local assemblies that have a high probability of being present in the genome of the organism, wherein z>k; and bringing together the z-mers in the plurality of local assemblies. Z can be between 100 and 300. The short-read sequence data can be generated from less than 10 ng of DNA input material. The short-read sequence data can be generated from less than 2 ng of DNA input material. In certain instances, the assembly is completed in less than 60 minutes. In some embodiments, the assembly can be completed in less than 60 minutes. In these embodiments, the one or more computers can comprise less than 512 GB of storage; in certain embodiments the one or more computers can comprise less than 60 GB of storage. In certain instances, the assembly is completed in less than 20 minutes. In these instances, the one or more computers comprise less than 512 GB of storage. In certain instances, the one or more computers comprise less than 60 GB of storage. In certain instances, the organism is a human being. In certain instances, the DNA sequence data is whole genome sequence data and the phased genome assembly is a whole genome assembly. In certain instances, the digital processing device occupies one cubic foot or less of physical space.

BRIEF DESCRIPTION OF THE DRAWINGS

FIG. 1 shows a non-limiting example of an alignment generated using the methods of this disclosure which preserves information regarding both SNPs and structural variants (SEQ ID NOS 1-8, respectively, in order of appearance).

FIG. 8 shows a non-limiting example of preponderance of errors near long homopolymers (SEQ ID NOS 9-24, respectively, in order of appearance).

DETAILED DESCRIPTION OF THE INVENTION

Certain Definitions

Figure 2:
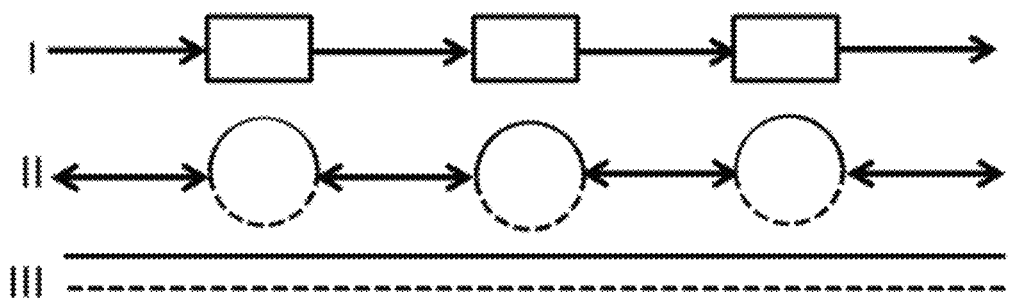
FIG. 2 shows a non-limiting example of a genomic assembly process.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, a "phased" assembly or sequence refers to creating an assembly where nucleotide data is accurately placed in cis at a particular locus such as a chromosome or other subgenomic interval. This could include for example properly resolving a haplotype, diploid genome, polyploid genome, different samples, different cells, different organisms, or even structural variants of a haploid genome such as large indels, translocations, and fusions.

As used herein, "next-generation sequencing" refers to any technology that results in large amounts nucleotide sequence data, generally greater than 1 gigabase in a 24-hour period. No limiting exemplar systems are available from Illumina (San Diego, Calif.), Life Technologies (Carlsbad, Calif.), and Pacific Biosystems (Menlo Park, Calif.).

Advantages of De Novo Assembly

The present disclosure is directed to novel approaches for obtaining and analyzing genomic information from biological samples that allow for improved genetic assembly of the sequence data so derived. In particular, the methods, systems, and media described herein involve the preparation of sequencing libraries that are encoded to preserve long range sequence context of individual, and much shorter stretches of determined sequence information as output by a given sequence system (referred to herein as "reads"). This long-range sequence context allows for the ordering of reads, regardless of length, over much longer sequence contexts than the length of the individual reads, e.g., 2×, 5×, 10×, 100×, 1000×, or even longer contiguous sequence stretches, as well as any range of lengths between these. Such long range contexts can be over contiguous sequence stretches that are on the order of 10 kb, 100 kb, 200 kb, 500 kb, 1 Mb, 2 Mb, 3 Mb, 4 Mb, 5 Mb, or even longer, as well as any range of lengths between these.

By providing such long-range sequence context, one can identify sequence characteristics that can generally be derived from long contiguous stretches of sequence, such as identifying large scale structural variations, determining haplotype information, and the like. All of these benefits are particularly useful in being able to accurately assemble true genome sequences, and moreover, true diploid or polyploid genome sequences, whether operating from a reference sequence or assembling the particular diploid genome, de novo. The platforms, systems, media, and methods described herein provide benefits that have been lacking in prior sequencing and de novo assembly processes, including use of: (i) very small amounts of input, (ii) lower sequence coverage, (iii) low cost, and (iv) computational efficiency.

The platforms, systems, media, and methods described herein allow assembly of a single sequencing library into a complete genome. A sequencing library is created beginning with a DNA sample that contains at least one entire genome, chromosome, or fragment of DNA. The DNA is then prepared by segmenting the DNA into large fragments typically greater than 1 kilobase, often greater than 10, 50, or 100 kilobases. These segments are then physically partitioned with each partition comprising a DNA fragment and a unique barcode or tag that serves to identify the DNA fragment, and any smaller fragments that are generated from the larger fragment. The barcode can be included on an oligonucleotide. The oligonucleotide can be releasably connected to a solid structure such as a bead or microcapsule. In some embodiments, the oligonucleotide can comprise a random sequence, a sequence complimentary to a target sequence, a sequence from a primer to attach, or a universal priming site.

Once the large DNA fragments are partitioned with a unique tag, smaller fragments are generated that incorporate the tag, which are then pooled into a library and sequenced. The library can be sequenced by any next-generation sequencing technology. In certain embodiments, the DNA sequence data is generated, by way of non-limiting examples, by pyrosequencing, sequencing by synthesis, sequencing by ligation, ion semiconductor sequencing, or single molecule real time sequencing. In certain embodiments, the DNA sequence data is generated by any technology capable of generating 1 gigabase of nucleotide reads per 24-hour period.

With possession of the sequence data from the reads of the various fragments and their associated barcode sequences, an assembly of a much larger sequence can be performed de novo. The sequencing reaction and the assembly step need not be carried out by the same individual or entity. The sequence data can be obtained from a third party. As described herein, this may be accomplished in a manner that preserves computational efficiency while permitting complex assembly processes to be completed. Exemplary methods of segmenting, partitioning, and tagging nucleic acid molecules are described in U.S. patent application Ser. No. 14/175,935, the full disclosure of which is hereby incorporated by reference in their entirety.

To call variants of all types, in principle one could align the assembly to the reference sequence, and then read off the variants. Aligning an assembly has tremendously greater specificity than aligning reads, thus eliminating most artifacts associated with standard reference-based analyses. FIG. 1 is an example from the HGP assembly. It shows a SNP, two small insertions and a 554 base insertion on one allele. The other allele shows the same insertion. There are no BLAST hits to GenBank. If you look at NA12878 instead, the same insertion is found, but only on one allele.

Computational Efficiency

When assembling genomic context from short-read sequence data, the ultimate assembly is a consensus assembly of samples, cells, or of different haplotypes/chromosomes. As such, creating a true diploid assembly of a genome even from long range sequences has to date been largely impossible. In particular, these assemblies typically may present an average assembly of a diploid genome, rather than specifically identifying haploid variants. In accordance with the methods described herein, one can obtain separate assemblies of different variants of otherwise homologous loci, e.g., from each haplotype, chromosome, cell, or sample.

Conventional assembly processes, due to the nature of shorter sequence reads and the computationally intensive assembly processes, place tremendous stress on computational infrastructures. In some cases, as described herein, processes are employed that have significantly more efficient computational processes than those conventionally used. In particular, in the processes described herein, an initial assembly graph is prepared. This initial assembly amounts to a "rough sketch" assembly and temporarily ignores areas of unresolved complexity, e.g., regions that may be ambiguous upon first glance, thus, preserving computing power. Once this initial assembly is created, areas of ambiguity may then be further processed by employing the barcoded sequencing data to create an accurate assembly of the areas of ambiguity. This allows k-mers derived from sequencing reads created during the assembly process to be addressable to a certain chromosome, cell, population, haplotype, etc. This allows efficient resolution of ambiguity—by reducing overall complexity in the assembly—conserving computational resources such as RAM, ROM, or processor cycles. In certain embodiments, the methods described herein, can reduce the amount of RAM necessary for assembly to below 512, 256, 128, 64, 32, 16, 8, or 4 gigabytes.

Using barcoded segmented nucleic acids contributes to the efficient assembly of genome sequences by contextualizing k-mers derived from sequence reads. By way of example, in a conventional assembly process not employing barcodes, following cleaning of the global assembly, most loci in the global assembly will represent two or more chromosomal loci (e.g., a maternally inherited and a paternally inherited chromosome). Using the barcodes, these loci are now separated from each other. This process will separate homologous chromosomes and also resolve complex segmental duplications. This is schematically illustrated in FIG. 2. As shown, a partially assembled sequence is illustrated with unassembled portion or portions, denoted by the boxes (step I). Neighborhood assembly is used to exploit the barcoded or tagged adjacent sequences to reach into the black box to provide assembly of the sequence therein. Moreover, where that sequence represents differing haplotype or phased sequence information, e.g., as shown by the dual arrows (step II), these barcodes will inform that as well, yielding, e.g., the separate variant assemblies within these regions. From the separate assemblies, one can generate true diploid assemblies at homologous loci (step III). The barcoded reads are placed back on the assembly and loci are identified whose exact sequence is not known with certainty, and so marked. The global assembly graph is now aligned to a reference sequence. First edges are aligned individually. Where these alignments are inconsistent (at points where two edges meet), the inconsistency is resolved by aligning the concatenations of these edges. The reference alignments together with quality markups now imply presence or absence of particular alleles for variants of all types (single base and structural)—and uncertainty where warranted. This is the "correct" version of variant calling attempted by traditional reference-centric approaches. Two or more related samples may be assembled together, yielding a single graph, from which the precise relationship between the samples at each locus may be inferred. This includes the case of tumor and normal (e.g., from one mixed clinical sample), and the case of de novo mutations in a child, seen by sequencing a family, including recombinations. Direct comparisons will reveal differences in loci that are absent from the reference sequence.

In certain implementations, described herein, an initial de novo assembly is created using short-read nucleotide sequencing technology. This de novo assembly can be based upon short-read sequence data. The short-read sequence data may be from reads of less than 300, 250, 200, 150, 100, 75, or 50 base pairs, including increments therein. The short-read sequence data may be from paired end reads. An initial de novo assembly graph may be created in a fashion that results in memory usage being small compared to the genome size. This optimizes the speed of the initial assembly. Memory usage does not increase proportionally with input data amount. The keys to the technologies are:
  (a) Based on frequency and base quality scores, k-mers are identified that have a high probability of being present in the genome—thus the number of these k-mers are dictated by the genome size.
  (b) K-mers are naturally coalesced during generation by bringing together those k-mers sharing a common minimum p-mer (p<k)—this reduces memory usage by an order of magnitude.
  (c) Subsequent assembly operations treat the initial assembly as an interim "reference sequence" and thus have very low memory requirements.

Given an edge e in the assembly, representing an unbranched sequence in the sample, its neighboring edges are found—these are the edges sharing a minimum number of barcodes with e. In certain embodiments the edges share at least 1, 2, 3, 4, 5, 6, 7, 8, 9, or 10 barcode sequences. These sequences are then assembled contiguously, yielding local assemblies (neighborhoods). This process also fills in gaps that were missing from the initial assembly. All neighborhoods are then assembled using a very large k-mer value. The resulting assembly is again a graph. The global assembly is now cleaned by removing connections inconsistent with the barcodes.

Assembly Method

K-mers that are generated from short sequence reads (read k-mers), approximate the graph that would be obtained by collapsing the sample genome along perfect k-mer matches. Prefiltering can be performed to exclude read k-mers that are likely wrong because, for example, they occur in only one barcode, or have low quality scores or are infrequent in the reads. Then, an initial graph is constructed from the k-mers. The edges of this graph are labeled with DNA sequences, representing unbranched paths (called "unipaths") in a De Bruijn graph. Next, patch gaps may be performed on this graph. Finally, "hanging ends" may be trimmed from the graph, yielding an initial assembly.

Read k-mers used to assemble the initial assembly can be any length that facilitates assembly, and may vary dependent upon the size of the genome being assembled. The read k-mer can be greater than 1, 10, 20, 30, 40, 40, 60, 70, 80, 90, or 100 base pairs, including increments therein. In certain instances, the read k-mer can be less than 10, 20, 30, 40, 40, 60, 70, 80, 90, or 100, base pairs in length, including increments therein. Generally, a k-mer between 30 and 50 base pairs is ideal for the initial de novo assembly. In certain instances, the k-mer may be between 40 and 50 base pairs. The k-mer may be 40, 41, 42, 43, 44, 45, 46, 47, 48, 59, or 50 base pairs in length. Ideally the k-mer is a multiple of four.

After the initial assembly is created a new global assembly (super graph) is constructed. The super graph's edges are labeled by paths in the initial assembly (and are thus represented as sequences of integers). Formally this graph has the same K value as in the initial assembly, but is resolved to a higher K value. This is achieved by finding paths in the base graph that are closures of read pairs, which therefore have length of approximately 100, 200, 300, 400, or 500 k-mers. These paths are formally aligned along long perfect overlaps to yield the super graph. These second larger k-mers are denoted as z-mers.

Figure 3:
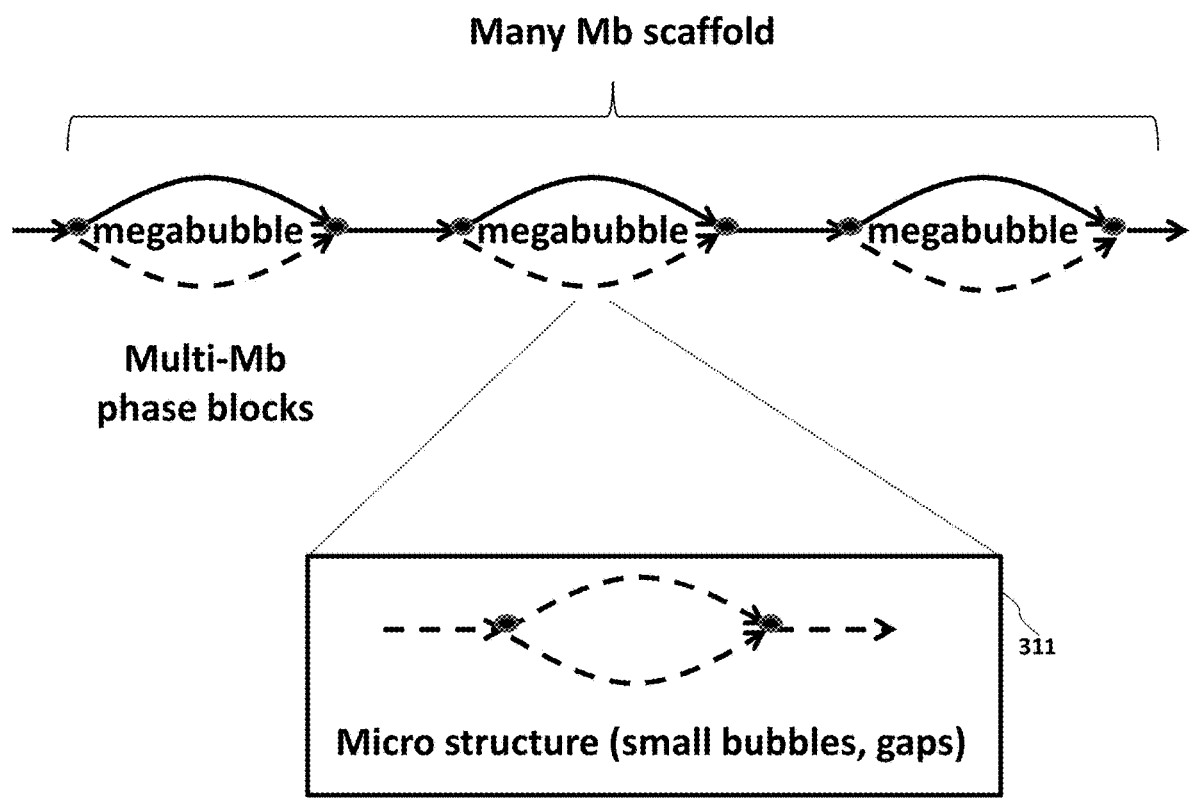
FIG. 3 shows a non-limiting example of alternative schematic illustration of a genomic assembly process with megabubbles and microstructure.
Figure 4:
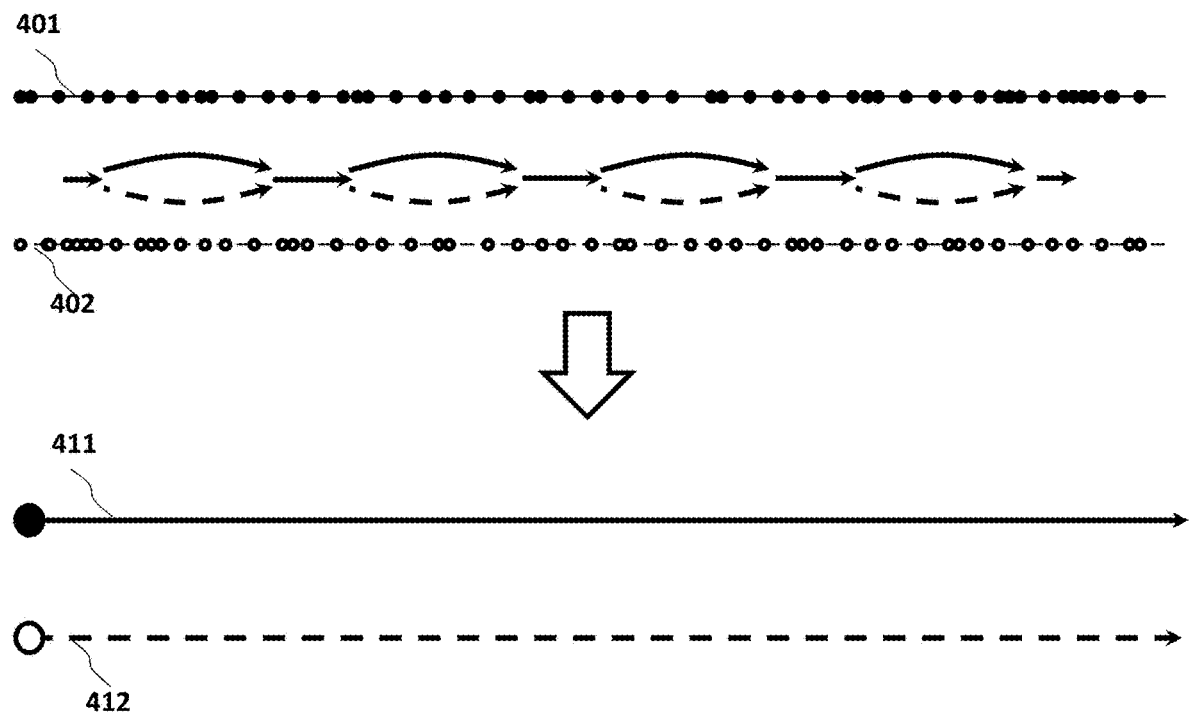
FIG. 4 shows a non-limiting example of a genomic assembly process.

After the global assembly the barcodes are used to locate and fill gaps. Gaps can be visualized as divergent "bubbles" due to a branch point in the unipath of the De Bruijn graph. Referring to FIG. 3, each scaffold has megabubbles, representing fully phased portions of the assembly. Successive megabubbles are not phased relative to one another. In general, each edge shown in the scaffold diagram contains within its "micro-structure," describing sequences that are not fully determined. These bubbles as shown if FIG. 3 can be derived from different contexts of the reads from which the k-mers are generated. The different contexts could be different chromosomes, samples or structural variants such as indels, duplications and translocations. The barcodes allow inference of a pool of reads that should cover a gap in the assembly, comprising of all the reads with a certain barcode sequence. After creating a local assembly from this pool, it can be reinserted into the global assembly. This is exemplified in FIG. 4 where one parental allele is in solid dotted line 401, while the other is in circle dotted line 402. Shown is one barcoded molecule landing on all the alleles in solid dots, and one landing on all alleles in circle dots, thus pulling them apart as 411 and 412, and thus properly phasing the sequence context. In reality, many barcoded molecules collude to execute this phasing operation. In certain embodiments, the methods described herein can create phased blocks of nucleotide sequence comprising over 1, 2, 3, 4, 5, 6, 7, 8, 9, 10 or more megabases. These levels of phasing can be achieved at coverage levels of 50× or below, 40× or below, or 30× or below for a 3 gigabase (human) genome.

Output

Figure 5:
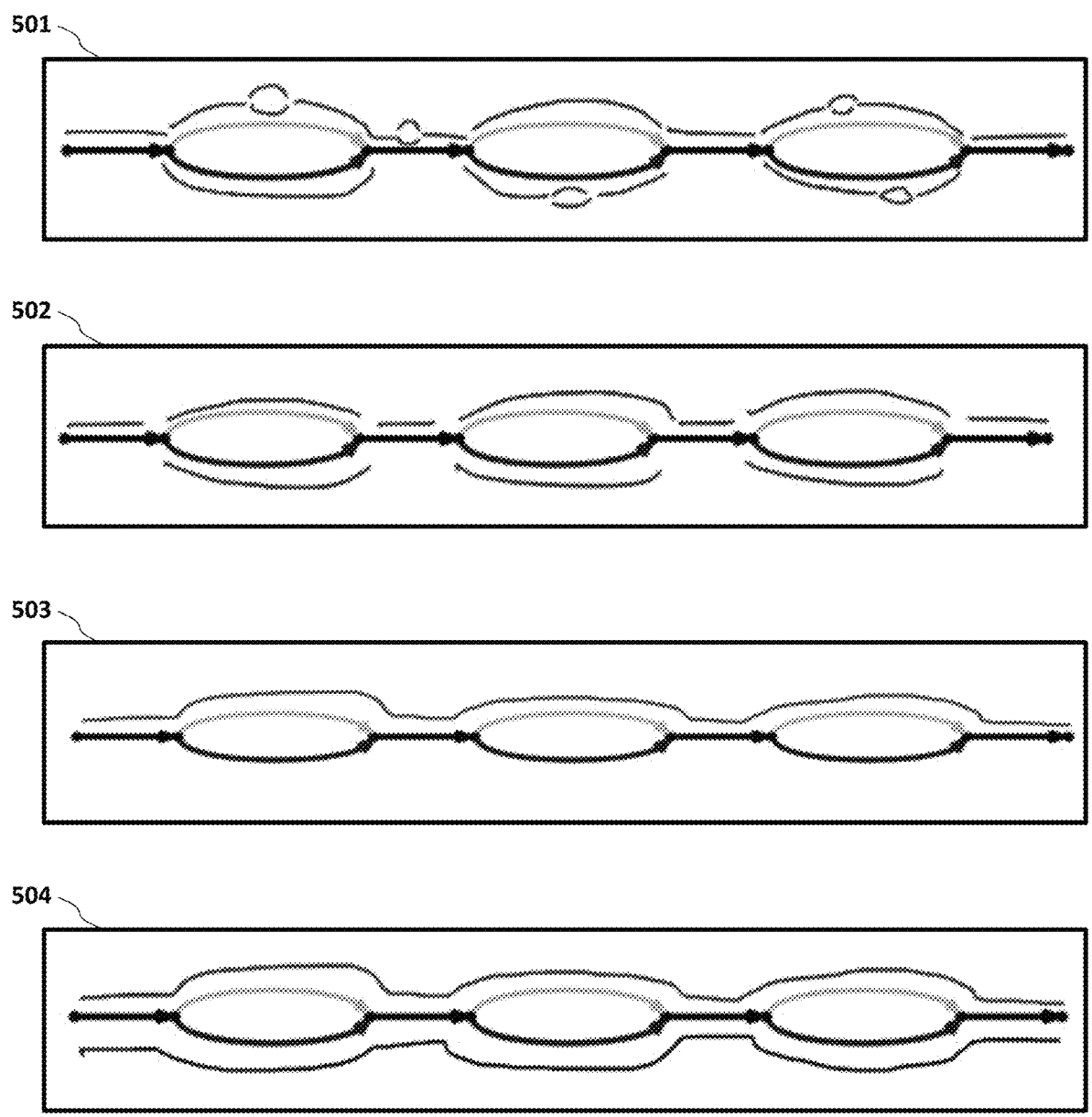
FIG. 5 shows a non-limiting example of outputs available from the genomic assembly process.

Referring to FIG. 5 the algorithm can output information to a user in many ways. Output 501 shows that data can be output in a "raw" style wherein very assembly edge (including microbubble arms and gaps) appears as a separate FASTA record. This is how the software sees the assembly. Output 502 shows that data can be output in a "megabubble style" wherein each megabubble arm corresponds to a single FASTA record, as does each intervening sequence. In some cases, the user can set a threshold to visualize megabubble or intervening sequences only if they occur over a certain stretch of the genome or exceed e a certain size threshold. Output 503 shows that data can be output in a "psuedohap style," a single record per scaffold. Megabubble arms are chosen arbitrarily so many records mix maternal and paternal alleles. Output 504 shows that data can be output in a "psuedohap2 style," wherein, for each scaffold, two "parallel" pseudo-haplotypes are created and placed in separate FASTA files.

Digital Processing Device

The methods, systems, and media described herein include at least one digital processing device, or use of the same. The digital processing device includes one or more hardware central processing units (CPUs) or general purpose graphics processing units (GPGPUs) that carry out the device's functions. The digital processing device further comprises an operating system configured to perform executable instructions. The digital processing device is optionally connected a computer network. By way of example, the digital processing device is optionally connected to the Internet such that it accesses the World Wide Web. By way of further example, the digital processing device is optionally connected to a cloud computing infrastructure. By way of further example, the digital processing device is optionally connected to an intranet. By way of still further example, the digital processing device is optionally connected to a data storage device.

In accordance with the description herein, suitable digital processing devices include, by way of non-limiting examples, commercial server computers and desktop computers known to those of skill in the art. Suitable digital processing devices also include devices custom-built using hardware and techniques known to those of skill in the art.

The digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some cases, the operating system is provided by cloud computing.

The device includes a storage and/or memory device. The storage and/or memory device is one or more physical apparatuses used to store data or programs on a temporary or permanent basis. In some embodiments, the device is volatile memory and requires power to maintain stored information. In some cases, the device is non-volatile memory and retains stored information when the digital processing device is not powered. The non-volatile memory may comprise flash memory, dynamic random-access memory (DRAM), ferroelectric random access memory (FRAM), phase-change random access memory (PRAM), or the like. In other cases, the device is a storage device including, by way of non-limiting examples, CD-ROMs, DVDs, flash memory devices, magnetic disk drives, magnetic tapes drives, optical disk drives, cloud computing-based storage, and the like. In various cases, the storage and/or memory device is a combination of devices such as those disclosed herein.

The digital processing device optionally includes a display to send visual information to a user. Suitable displays include liquid crystal displays (LCD), thin film transistor liquid crystal displays (TFT-LCD), organic light emitting diode (OLED) displays (including passive-matrix OLED (PMOLED) and active-matrix OLED (AMOLED) displays), plasma displays, video projectors, and head-mounted displays (such as a VR headset) in communication with the digital processing device. Suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In various cases, the display is a combination of devices such as those disclosed herein.

The digital processing device optionally includes one or more input devices to receive information from a user. Suitable input devices include keyboards, pointing devices (including, by way of non-limiting examples, a mouse, a trackball, a track pad, a joystick, a game controller, and a stylus), touch screens or a multi-touch screens, microphones to capture voice or other sound input, video cameras or other sensors to capture motion or visual input. In particular cases, the input device is a Kinect, Leap Motion, or the like. In various cases, the input device is a combination of devices such as those disclosed herein.

Figure 6:
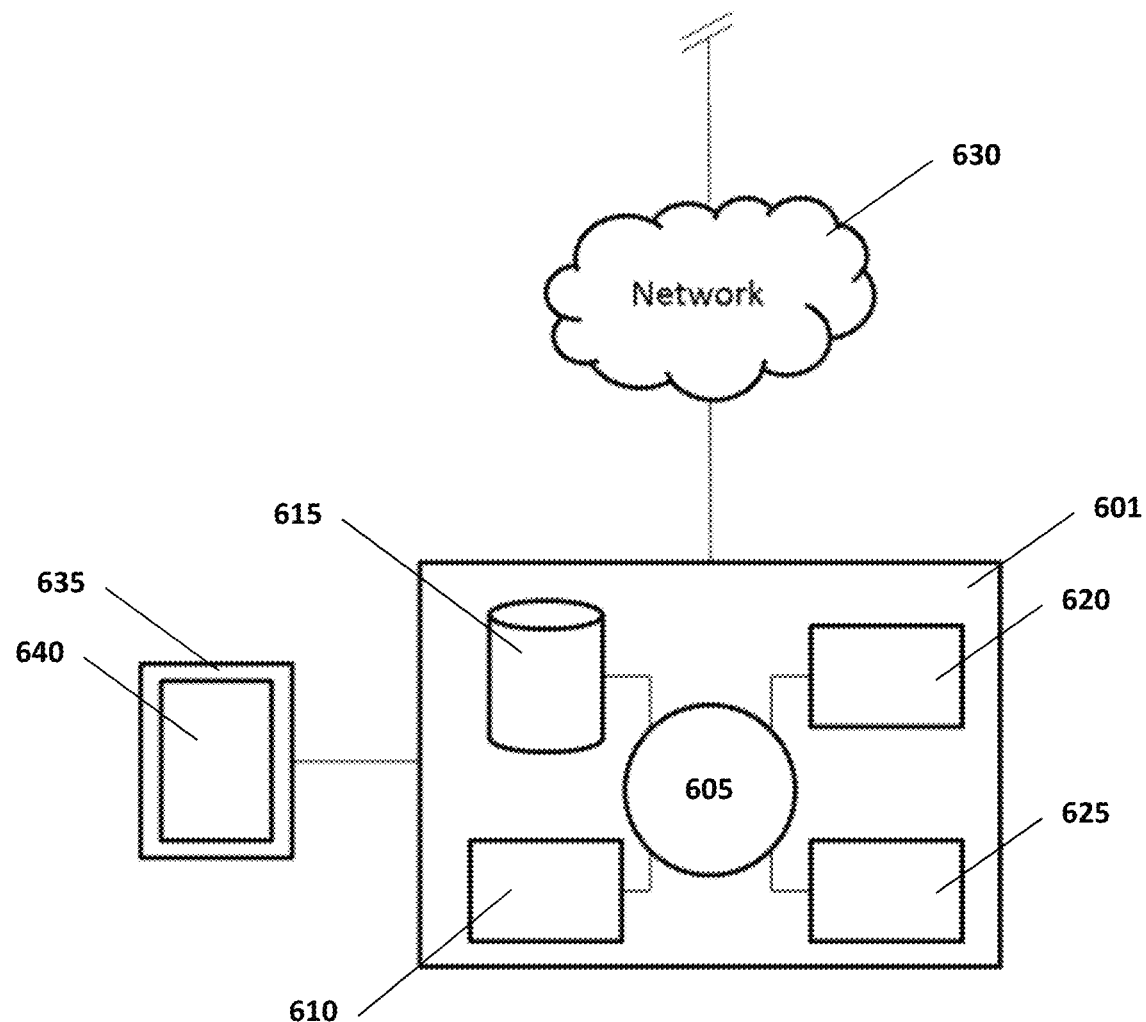
FIG. 6 shows a non-limiting example of a digital processing device; in this case, a device with one or more CPUs, a memory, a communication interface, and a display.

Referring to FIG. 6, in a particular embodiment, an exemplary digital processing device 601 is programmed or otherwise configured to assemble short-read DNA sequences into fully phased complete genomic sequences. The device 601 can regulate various aspects of the sequence assembly methods of the present disclosure, such as, for example, performing initial alignments, quality checking, performing subsequent alignments, resolving ambiguity, and phasing heterozygous loci. In this embodiment, the digital processing device 601 includes a central processing unit (CPU, also "processor" and "computer processor" herein) 605, which can be a single core or multi core processor, or a plurality of processors for parallel processing. The digital processing device 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 525, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The digital processing device 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the device 601, can implement a peer-to-peer network, which may enable devices coupled to the device 601 to behave as a client or a server.

Continuing to refer to FIG. 6, the CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and write back. The CPU 605 can be part of a circuit, such as an integrated circuit. One or more other components of the device 601 can be included in the circuit. In some cases, the circuit is an application specific integrated circuit (ASIC) or a field programmable gate array (FPGA).

Continuing to refer to FIG. 6, the storage unit 615 can store files, such as drivers, libraries and saved programs. The storage unit 615 can store user data, e.g., user preferences and user programs. The digital processing device 601 in some cases can include one or more additional data storage units that are external, such as located on a remote server that is in communication through an intranet or the Internet.

Continuing to refer to FIG. 6, the digital processing device 601 can communicate with one or more remote computer systems through the network 630. For instance, the device 601 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

Non-Transitory Computer Readable Storage Medium

The methods, systems, and media disclosed herein include one or more non-transitory computer readable storage media encoded with a program including instructions executable by the operating system of an optionally networked digital processing device. In some cases, a computer readable storage medium is a tangible component of a digital processing device. In other cases, a computer readable storage medium is optionally removable from a digital processing device. A computer readable storage medium includes, by way of non-limiting examples, CD-ROMs, DVDs, flash memory devices, solid state memory, magnetic disk drives, magnetic tape drives; optical disk drives, cloud computing systems and services, and the like. In some cases, the program and instructions are permanently, substantially permanently, semi-permanently, or non-transitorily encoded on the media.

Computer Program

The methods, systems, and media disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some cases, a computer program comprises one sequence of instructions. In other cases, a computer program comprises a plurality of sequences of instructions. In some cases, a computer program is provided from one location. In other cases, a computer program is provided from a plurality of locations. In various cases, a computer program includes one or more software modules. In various implementations, a computer program includes, in part or in whole, one or more web applications, one or more mobile applications, one or more standalone applications, one or more web browser plug-ins, extensions, add-ins, or add-ons, or combinations thereof.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some cases, a computer program includes one or more executable compiled applications.

Software Modules

The methods, systems, and media disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various implementations, a software module comprises a file, a section of code, a programming object, a programming structure, or combinations thereof. In other various implementations, a software module comprises a plurality of files, a plurality of sections of code, a plurality of programming objects, a plurality of programming structures, or combinations thereof. By way of non-limiting examples, the one or more software modules comprise a web application, a mobile application, and a standalone application. In some cases, software modules are in one computer program or application. In other cases, software modules are in more than one computer program or application. In some cases, software modules are hosted on one machine. In other cases, software modules are hosted on more than one machine. In particular cases, software modules are hosted on one or more cloud computing platforms and/or services. In some cases, software modules are hosted on one or more machines in one location. In other cases, software modules are hosted on one or more machines in more than one location.

Databases

The methods, systems, and media disclosed herein include one or more databases, or use of the same. In view of the disclosure provided herein, those of skill in the art will recognize that many databases are suitable for storage and retrieval of sequence and graph information. Suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some cases, a database is internet-based. In further cases, a database is web-based. In still further cases, a database is cloud computing-based. In other cases, a database is based on one or more local computer storage devices.

EXAMPLES

The following illustrative examples are representative of embodiments of the software applications, systems, and methods described herein and are not meant to be limiting in any way.

Example 1—Diploid De Novo Sequence Assembly Using Tagged Reads Generates Long Stretches of Genomic Phasing To thoroughly test the methods of this disclosure on different genomes, this example generated datasets from seven individuals of varied ancestry and sex and three mixed breed dogs as shown in Table 1. These datasets demonstrate genomes of sizes 3.2 and 2.5 Gb, respectively. All were created from DNA of size ≥80 kb.

TABLE 1

| | | | | | | | continuity | | |
|---|---|---|---|---|---|---|---|---|---|
| | | input | | | | | N50 | N50 phase | N50 |
| ID | sample | ethnicity | sex | data description | X | F | contig (kb) | block (Mb) | scaffold (Mb) |
| A | NA19238 | Yoruban | F | one 10X library | 56 | 115 | 114.6 | 8.0 | 18.7 |
| B | NA19240 | Yoruban | M | one 10X library | 56 | 125 | 118.8 | 9.3 | 16.4 |
| C | HG00733 | Puerto Rican | F | one 10X library | 56 | 106 | 124.4 | 3.4 | 17.7 |
| D | HG00512 | Chinese | M | one 10X library | 56 | 102 | 113.2 | 2.8 | 15.4 |
| E | NA24385 | Ashkenazi | M | one 10X library | 56 | 120 | 106.7 | 4.3 | 15.0 |
| F | HGP | European | M | one 10X library | 56 | 139 | 120.2 | 4.5 | 18.6 |
| G | NA12878 | European | F | one 10X library | 56 | 92 | 119.7 | 2.7 | 17.5 |
| H | NA12878 | European | F | unknown number of PacBio libraries plus BioNano Genomics date[42] | 46 | / | 1594.2 | / | 25.4 |
| I | NA12878 | European | F | 6 libraries (fragment, jumping, 10X)[43] | 160 | / | 12.3 | / | 30.1 |
| J | NA12878 | European | F | 9 libraries (fragment, jumping, Fosmid, HiRise)[DOVE] | 150 | / | 43.6 | / | 42.8 |
| K | NA24385 | Ashkenazi | M | 7 PacBio libraries | 71 | / | 4525.2 | / | 4.5 |
| L | NA24143 | Ashkenazi | F | 2 PacBio libraries | 30 | / | 1048.4 | / | 1.0 |
| M | YH | Chinese | M | ~18,000 Fosmid pools and 6 fragment and jumping libraries, Illumina sequenced, plus Complete Genomics data[YH] | 702 | / | 52.5 | 0.5 | 23.2 |
| N | Cuishle | Goldendoodle | M | one 10X library | 56 | 90 | 72.2 | 4.3 | 11.4 |
| O | Ollie | mutt | M | one 10X library | 56 | 83 | 64.6 | 4.9 | 12.2 |
| P | Ruby | mutt | F | one 10X library | 56 | 84 | 73.0 | 2.9 | 12.8 |

TABLE 1-continued

| | | | | comparison to truth data | | | | |
|---|---|---|---|---|---|---|---|---|
| | | | | reference | | | | |
| | continuity | same N50 perfect | parental | missinG k-mers | | discrepant at given distance (%) | | run time wall |
| input ID | gappi-ness | stretch (kb) | phasing error % | (%) haploid | diploid | 1 Mb | 10 Mb | clock (days) |
|---|---|---|---|---|---|---|---|---|
| A | 2.1 | / | / | 14.4 | 10.0 | 1.3 | 0.8 | 2.1 |
| B | 2.3 | / | 0.086 | 14.9 | 10.4 | 1.3 | 0.7 | |
| C | 2.0 | / | 0.089 | 13.2 | 9.8 | 1.0 | 1.3 | 2.2 |
| D | 2.2 | / | / | 13.5 | 10.0 | 1.4 | 0.5 | 1.9 |
| E | 2.6 | / | 0.053 | 14.0 | 9.6 | 1.3 | 0.7 | 2.1 |
| F | 2.5 | 19.1 | / | 12.3 | 8.8 | 1.9 | 0.9 | / |
| G | 1.9 | 18.7 | 0.018 | 13.2 | 9.7 | 1.0 | 0.6 | 2.5 |
| H | 4.6 | / | / | 18.0 | / | 0.5 | 2.0 | / |
| I | 10.2 | / | / | 19.7 | / | 1.1 | 7.1 | / |
| J | 0.6 | / | / | 14.8 | / | 5.6 | 6.0 | / |
| K | 0.0 | / | / | 11.8 | / | 2.2 | 17.9 | / |
| L | 0.0 | / | / | 14.3 | / | 15.2 | N/A | / |
| M | 1.5 | / | / | / | 10.4 | 1.2 | 1.6 | / |
| N | / | / | / | / | / | / | / | 1.4 |
| O | / | / | / | / | / | / | / | 1.5 |
| P | / | / | / | / | / | / | / | 1.3 |

Table 1 Legend: All statistics were computed after removing scaffolds shorter than 10 kb. Comparisons to reference use GRCh37 (chr1-22,X,Y), with chrY excluded for female samples. ID: identifier of assembly in this table. Sample: type of starting material. HGP is from the living anonymous donor to the Human Genome Project for libraries RPCI 1,3,4,5 (available at http://bacpac.chori.org/library.php?id=1), for which 340 Mb of finished sequence are in GenBank. Dogs and HGP were from blood, others are Coriell cell lines. Ethnicity: ethnicity, or for dogs, breed origin. Sex: sex of sample. Data description: capsule description of data type. X: estimated coverage of genome by sequence reads. For assemblies of this work, reads were 2×150; 1200M reads were used for each human assembly; 940M reads for each dog assembly; dogs and sample G were sequenced on HiSeq 2500 in rapid run mode; other samples were sequenced on HiSeq X. F: inferred length-weighted mean fragment length of DNA in kb. N50 contig size: N50 size of FASTA records, after breaking at sequence of 10 or more n or N characters. N50 scaffold size: N50 size of FASTA records, excluding Ns. Gappiness: fraction of bases that are ambiguous. N50 perfect stretch: N50 length in kb of segments on finished sequence from same sample that are perfectly mirrored in assembly (see text). Phasing error % at 1 Mb: fraction of phased sites in megabubble branches where phasing did not agree with the majority. Missing k-mers: fraction of 100 k-mers in reference that are missing from the assembly. Haploid: haploid version of assembly. Diploid: diploid version of assembly. Discrepant at given distance: of k-mers pairs at the given distance in the assembly, and for which both are uniquely placed on the reference, fraction for which either the reference chromosome, orientation, order, or separation (±10%) are inconsistent. Wall clock: run time (days) for assemblies using a single server having 384 GB available memory (booted with "mem=384G"), starting from FASTQ files.

Example 2—Generation of Sequencing Data

Nucleic acid preparation and generation of sequencing data has been previously described. Briefly, several million beads were used as input to a given library construction, with each bead containing many copies of a 14-base barcode unique to that bead. A microfluidic device delivers individual beads into approximately one million partitions, along with genomic DNA and reagents. Each partition contained several long fragments (as discussed below), and the system was arranged to create constructs having the barcode, along with ~300 bp of genomic DNA from a fragment sandwiched between Illumina adapters. The barcode was placed at the beginning of the first read in a pair.

Of the nucleic acid that is loaded, approximately 40% appears in the library. For example, if 1.25 ng of material is loaded, distributed across 106 partitions, and has a mean size of 50 kb, the mean number of molecules per partition would be about 10—representing ~0.5 Mb of genome per partition. At 56× coverage, the mean number of read pairs per molecule for a human genome would thus be (1200M/2)/(106×10)=60, and covering the molecule to depth (120*150)/(50,000)=0.36×.

For smaller genomes, and at the same fixed level of coverage (56×), the number of read pairs per molecule drops proportionally, which can reduce the power of the data type. For example, for a genome whose size is 1/10th the size of the human genome (320 Mb), the mean number of read pairs per molecule would be about 6, and the distance between read pairs would be about 8 kb, making it hard to anchor barcodes to short initial contigs.

These constructs are then sequenced on an Illumina instrument. Paired reads of length 150 bases each should be generated. This read length was chosen so that data could be sequenced on the HiSeq X instrument, which yields the lowest cost data among Illumina instruments, and which has a maximum read length of 150. Data can also be generated on the HiSeq 2500 in rapid run mode. We recommend that samples be sequenced to 56×, or about 1200M reads for a human genome, however, lower coverage is possible and described later.

Example 3—Assemblies Using Nucleic Acids of Differing Size

The performance of the system was tested on DNA of several different sizes, showing that DNA length is an important factor. The data in Table 2 show assembly performance on data from four different libraries, constructed from NA12878 DNA of various lengths, and sequenced to 38× coverage. Particularly for DNA<30 kb, data showed that a DNA of size ~20 kb yielded scaffolds of N50 size 0.6 Mb, whereas DNA of size ~50 kb yielded scaffolds of size N50 12.8 Mb.

TABLE 2

| DNA length estimates (kb) | | Output statistics | | | |
|---|---|---|---|---|---|
| From gel measurement | Length weighted mean, from Supernova | N50 perfect stretch (kb) | N50 contig (kb) | N50 phase block (Mb) | N50 scaffold (Mb) |
| 13 | 14 | 2.0 | 14.2 | 0.0 | 0.0 |
| 20 | 21 | 7.9 | 61.4 | 0.1 | 0.6 |
| 30 | 35 | 9.0 | 78.1 | 0.3 | 9.6 |
| 68 | 48 | 8.3 | 86.9 | 0.5 | 12.8 |

Example 4—Assemblies of HGP Sample at Varied Coverage

Additionally, sequencing and assembly of the human genome project donor sample was performed at varying coverage. Table 3 shows that large phase blocks of at least 2.3 megabases can be generated from 38× sequence coverage.

TABLE 3

Assemblies of HGP sample at varied coverage

| Coverage (x) | N50 contig (kb) | N50 phase block (Mb) | N50 scaffold (Mb) | N50 perfect stretch (kb) |
|---|---|---|---|---|
| 38 | 89.8 | 2.3 | 13.5 | 11.8 |
| 47 | 95.0 | 3.3 | 14.0 | 15.1 |
| 56 | 95.2 | 4.1 | 13.4 | 16.9 |

Example 5—De Novo Assembly

Barcoded data provides shallow coverage of each molecule, it is not possible to start the assembly process by separately assembling the reads in each partition (which otherwise would be a natural approach). Instead in this example, the assembly process proceeds by building progressively larger assembly units. Once these units are a few kb long, the probability that a given unit overlapped reads from a given molecule (at the same locus) is high, and it is thus possible to identify many of the barcodes that are incident upon the unit, hence to group the barcodes, and hence assemble groups. This is an analog of separately assembling reads from each partition.

The Supernova algorithm follows this, thus deferring major use of barcodes. To start out, a De Bruijn graph algorithm was approached, adapting the method of DISCO-VAR to scale to whole genome datasets and exploit barcoded data. K-mers (K=48 in some embodiments) were pre-filtered to remove those present in only one barcode, thus reducing the incidence of false k-mers, i.e., those absent from the sample. The remaining k-mers were formed into an initial directed graph, in which edges represented unbranched DNA sequences, and abutting edges overlapped by K−1 bases. Operations were then carried out to recover missing k-mers and remove residual false k-mers. At this point the graph (called the base graph) is an approximation to what would be obtained by collapsing the true sample genome sequence along perfect 48-mer repeats.

Next for each read pair, where possible, one path or sometimes more paths were found in the graph that could represent the sequence of the originating insert. These paths were represented as sequences of integers corresponding to the identifiers of edges in the base graph. Whenever there were two paths perfectly overlapping by K=200 bases, the paths formally joined via an equivalence relation. This yielded a new directed graph, called the super graph, whose edges were labeled by sequences of integers, representing paths in the base graph. Each super graph edge may be translated into a DNA sequence. Where super graph edges abutted, their associated sequences overlapped by K−1 bases (K=48 in this example). However the super graph represented an approximation to what would be obtained by collapsing the true sample genome sequence along perfect 200-mer repeats. It was thus far more resolved than the base graph.

Figure 7:
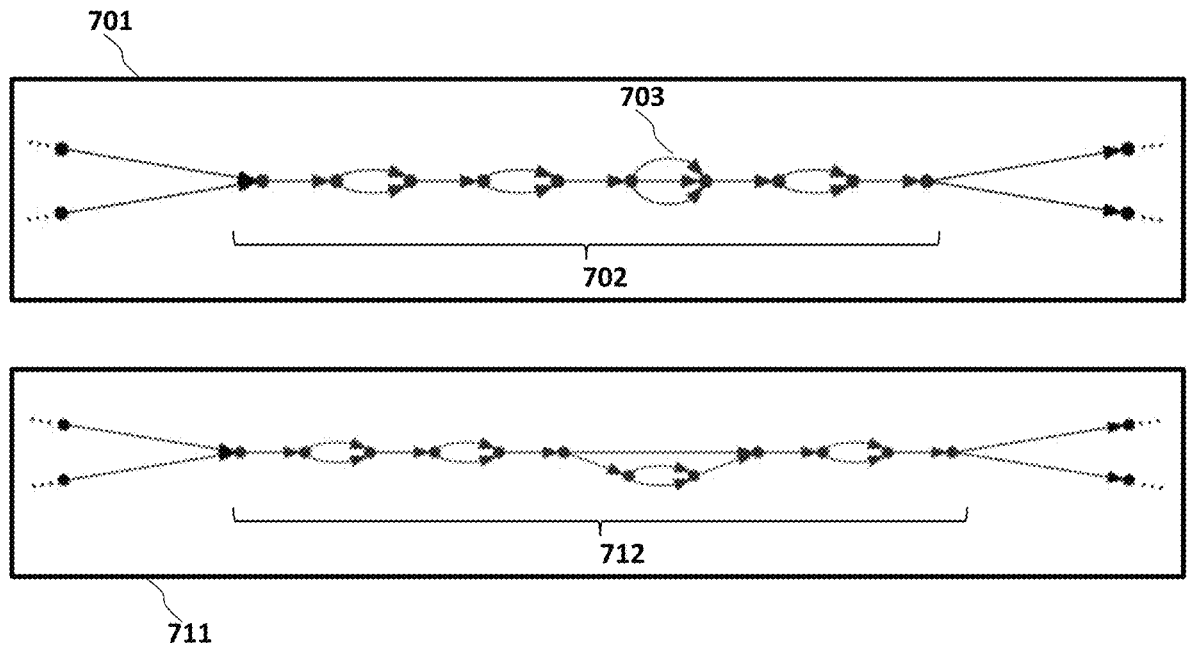
FIG. 7 shows a non-limiting example of de novo assembly.

The remainder of the assembly process consisted of a series of operations that modifies this graph, with the intention of improving it. To facilitate these operations and to understand the nature of individual assemblies, the graph was decomposed into units called lines. Referring to FIG. 7, lines were extended linear regions, punctuated only by "bubbles." Bubbles are places in the graph where the sequence diverges temporarily along alternate paths that then reconnected. Initially most arise from heterozygous sites in the genome. In FIG. 7, each edge represents a DNA sequence. In panel 701, the portion 702 describes a line in an assembly graph, which is an acyclic graph part bounded on both ends by single edges. The line alternates between five common segments and four bubbles, three of which have two branches. The third bubble 703 is more complicated. The entire graph may be partitioned so that each of its edges lies in a unique line (allowing for degenerate cases, including single edge lines, and circles). The panel 711 shows the line 712 identical to the line 702, but now each bubble has been replaced by a bubble consisting of all its paths. After this change, each bubble consists only of parallel edges.

One can use lines to scaffold the super graph. This involves determining the relative order and orientation of two lines, then breaking the connections at their ends, then inserting a special "gap" edge between the lines. The end result is a new line, which has a special "bubble" consisting only of a gap edge. Subsequent operations (described later) may remove some of these gaps, replacing them by sequence.

Scaffolding was first carried out using read pairs. If the right end of one line was unambiguously connected by read pairs to the left end of another line, then they could be connected. Read pairs can reach over short gaps.

To scaffold across larger gaps, barcodes were used. Briefly, if two lines were actually near each other in the genome, then with high probability, multiple molecules (in the partitions) bridged the gap between the two lines. Therefore for any line, one may find candidate lines in its neighborhood by looking for other lines sharing many of the same barcodes. Alternative orders and orientations (O&Os)

of these lines were then tested, judiciously restricting tests to small sets of lines to avoid a combinatorial explosion.

For all lines in the assembly, an initial computation was carried out. The computation assigned a linear coordinate system to each line and marks the positions of uniquely placed reads on it, organized by barcode. Now for a given line set S, one can score alternative O&O possibilities, as follows. Each O&O for S thus yielded a sequence of barcoded read positions along a hypothetical merged line. A score was computed for the given O&O, which was a sum, over all its constituent barcodes. For each barcode, first compute the mean separation between successive read placements for that barcode (in the merged line). Then, traversing these placements, in order, found those pairs of consecutive placements that bridged a jump from one constituent line to another, and which may thus represent a misconnection. The separation was divided for this pair by the mean separation for the barcode. If the quotient was smaller than a fixed bound, e.g., 2.0, it was discarded on the theory that it is probably noise. The remaining quotient was added to the score sum.

A given O&O was treated as the "winner" if its score was at least a fixed amount less than competing tested O&O possibilities for the same set of lines. On this basis, lines were scaffolded using barcodes.

Once the assembly had been scaffolded, some gaps may be filled in with sequence. For short gaps, read pairs from both sides of the gap reached in and may cover the intervening sequence, from which it may be inferred. For long gaps, first find the barcodes that were incident on sequence proximate to the left and right sides of the gap. Then, find all the reads in these barcodes. This set of reads would include reads that properly were within the gap, and yet be roughly ten times larger than that set (as each droplet contains about ten molecules). The full set of reads was assembled. Reads outside the gap locus tended to be at low coverage and hence not assemble. In this way it was typically possible to fill in the gap with a chunk of graph, and thereby remove the gap from the assembly. The chunk may not be a single sequence. For example at this stage heterozygous sites within the gap would typically be manifested as simple bubbles.

The final step in the assembly process was to phase lines. Referring FIG. 7, first for each line, one can find all its simple bubbles, i.e., bubbles having just two branches. Then, a set of molecules was defined. These were defined by series of reads from the same barcode, incident upon the line, and not having very large gaps (>100 kb).

A "phasing" is an orientation of each bubble, placing one branch on "top" and the other on the "bottom." Initially an arbitrary orientation was chosen. Each molecule touched some bubbles, and thus (relative to a given phasing) may be represented as a sequence with entries +1 for top, −1 for bottom, or 0 for silent. A phasing is "good" if each molecule is coherent, containing nearly all 1s or nearly all −1s (plus 0s at silent positions). Accordingly, the score of a phasing was defined to be the sum over all molecules of Max(pluses, minuses)-Min(pluses,minuses).

Then, this example carried out iterative perturbations, each of which flipped some bubbles, and kept only those perturbations that increased the phasing score, Three types of perturbations were attempted: (a) Flip bubbles on a given molecule to make it completely coherent; (b) Flip an individual bubble; and (c) Pivot at a given point, flipping all bubbles to its left.

Now came with an initial phasing. Then, one can consider weaknesses in it. First, if flipping a bubble had too small an effect on the score, it was excluded from the phasing operation. For example a bubble might arise at a long homopolymer whose length was fixed in the sample but changed during data generation. Second, if a pivot had too small an effect on the score, the phasing was broken at the pivot point, resulting in multiple phase blocks for a given scaffold. For example this could happen if a sufficiently long block in a given sample was homozygous.

In some applications, Supernova was designed to run on a single Linux server. For a human-sized genome, typical peak memory usage was 300 GB; it is recommended to use a server having ≥384 GB RAM. Wall clock run times are shown in Table 1. At fixed coverage, memory and run time were roughly linear as a function of genome size.

Example 6—Supernova Output

Again referring FIG. 3, a Supernova assembly can capture the biology of a diploid genome. Phase blocks appear as "megabubbles" with each branch representing one parental allele, whereas sequences between megabubbles are nominally homozygous. Successive megabubbles are not phased relative to each other (if they were, they would have been combined). A chain of megabubbles as shown comprise a given scaffold. In addition to large scale features, the Supernova graph encodes smaller features such as gaps and bubbles at long homopolymers whose length is not fully determined by the data. In FIG. 3, Supernova assemblies encode diploid genome architecture. Each edge represents a sequence. Megabubble arms represent alternative parental alleles at a given locus, whereas sequences between megabubbles are homozygous (or appear so to Supernova). Smaller scale features 311 appear as gaps and bubbles.

Again referring to FIG. 5, a Supernova assembly can be translated into FASTA in several distinct ways, which might prove useful for different applications. These allow representation of the full "raw" graph 501, or erase micro features (choosing the most likely branch at small bubbles and replacing gap edges by Ns). There is more than one way to package the result, depending on how megabubble branch points are handled in megabubble style 502, pseudohap style 503 and pseudohap2 style 504. Note that erasing micro features entails some loss of information, as in some cases the wrong branch of a bubble is chosen.

Cycles in the graph provide an interesting test case. A cycle means a set of one or more edges that comprise a cyclic part of the graph. These are left intact in the full graph, however in the other forms are replaced by a path through the cycle that traverses each edge at least once, followed by Ns. This unfortunately signifies a gap (which could in principle represent any sequence), whereas the full graph indicates precisely which sequences could be present at the locus.

FIG. 5 shows several styles. In 501, the raw style represents every edge in the assembly as a FASTA record (seen as red segments). These include microbubble arms and also gaps (printed as records comprising 100 Ns for gaps bridged by read pairs, or a larger number, the estimated gap size, Supp. Note 6). Unresolved cycles were replaced by a path through the cycle, followed by 10 Ns. Bubbles and gaps generally appear once per 10-20 kb. Raw graph records are roughly two orders of magnitude shorter than megabubble arms. For each edge in the raw graph, there is also an edge written to the FASTA file representing the reverse complement sequence. For the remaining output styles, we flatten each bubble by selecting the branch having highest coverage, merge gaps with adjacent sequences (leaving Ns), and drop reverse complement edges. In the second style 502, each megabubble arm corresponds to a FASTA record, as does each intervening sequence. The third style 503 is pseudohap style which generates a single record per scaffold. For example in the cartoon for style two, the seven red edges on top (corresponding to seven FASTA records) are combined into a single FASTA record. Megabubble arms are chosen arbitrarily so many records will mix maternal and paternal alleles. The fourth style 504 is like the pseudohap option, except that for each scaffold, two "parallel" pseudo-haplotypes are created and placed in separate FASTA files.

Example 7—Inferred DNA Length

For each of the assemblies, one could infer the statistics of DNA molecules that made it into a partition and were thence sequenced, thus reflecting the quality of input material and degradation during the initial steps of library construction. Table 1 shows the inferred values for the length-weighted mean (LWM) of these molecules, as field F. Dog DNA was in the range 83-90 kb whereas human DNA was in the range 92-139 kb. This difference might conceivably be attributable to differences in base composition, such as at CpG islands. All dog DNA was obtained from fresh blood, as was the longest human DNA sample. The other human samples were obtained from cell lines. The shortest human sample (NA12878) may have been shortest because of repeated handling of the DNA tube to create multiple libraries, as that DNA sample was used as a control for many experiments.

Example 8—Assessment of Human Assemblies

This example assessed seven assemblies and six human assemblies, encompassing a wide range of laboratory approaches, from low coverage (30×) PacBio to complex combinations of multiple technologies at much higher coverage (Table 1). For each assembly, several statistics were computed, to the extent that those statistics could be computed. Before computing these statistics, first step removed all scaffolds shorter than 10 kb from each assembly, thereby normalizing for differences in the actual cutoffs used in defining the assemblies, which would otherwise significantly affect statistics, including coverage of the genome.

To assess the continuity of the assemblies, the first step computed the N50 contig size. The mean across the seven Supernova assemblies was 117 kb, with little variation. The three assemblies based on PacBio had much larger contigs, whereas contigs from the other assemblies were two-fold or shorter than those from Supernova.

All of the Supernova assemblies were diploid, with N50 phase block size ranging from 2.7 to 10.7 Mb, with variability due presumably to varied ancestry and varied DNA length. Of the six other human assemblies, only the 702× assembly was diploid, and it had an N50 phase block size of 0.5 Mb. The large molecules underlying Linked-Reads enabled the long phase blocks that were difficult to achieve with other technologies.

Scaffolds in the Supernova assemblies ranged from 15 to 19 Mb (N50). While the PacBio-only assemblies had much shorter scaffolds, the four combination assemblies had longer scaffolds, ranging from 23 to 43 Mb. The gaps (fraction of Ns) in these scaffolds also varied greatly, from 0% for the PacBio assemblies, to 2% for the Supernova assemblies, to 10% for assembly I.

Any assessment of assembly continuity would be tempered by an assessment of the accuracy and completeness of those same assemblies. Although one could do this by comparing to a human reference sequence (and we do so later), the ideal would be to exploit ground truth data from the same sample that was assembled. These data would consist of clones that had been independently sequenced and assembled, and which were representative of the genome. One could find only two samples, for which such truth data was available and for which high quality DNA could be procured to create assemblies. These were the sample from a living Human Genome Project donor, for which 340 Mb of finished clones had been sequenced and assembled during the project, at great expense, and NA12878, which were previously sequenced and assembled 4 Mb of random clones. Although the HGP clones were not truly random, one reason was that they comprised so much of the genome (~10%) that they would be reasonably representative of it.

For a given sample, if the exact sequence was known for each of its chromosomes, one could assess the accuracy of an assembly of that sample by enumerating maximal regions of the genome that are perfectly represented in the assembly. Most such regions would be terminated by errors or gaps in the assembly. (Note that displaying the wrong allele would count as an error.) The N50 size of such perfectly represented regions was called the "N50 perfect stretch." For diploid genomes, if one has both a diploid assembly (thus attempting to display all chromosomes), and representative finished sequence from the exact same sample (thus providing a sample of those chromosomes), then one can approximate the N50 perfect stretch. Of the samples in Table 1, only assemblies F and G satisfy these requirements.

It was found that the N50 perfect stretch in these Supernova assemblies was about-19 kb (Table 1). Moreover, examination of the alignments of the finished sequence to the assembly reveals the exact nature of the assembly defects that terminate these perfect stretches. For example FIG. 8 (and the corresponding alignments for thousands of other clones) shows a preponderance of errors near long homopolymers, which might be attributable to library construction defects, sequencing defects, algorithmic defects, or possibly errors in the finished sequence. In more detail, FIG. 8 shows that inside a 162 kb region (interesting because it is subsumes a region of Neanderthal origin), there are seven discrepancies between the assembly and the finished sequence for the region (plus two gaps). One of the discrepancies is a single-base mismatch. Because all the assembly reads support the assembly sequence, it seems likely that the finished sequence is wrong in this instance (and not the Supernova assembly). In fact this site was corrected in GRCh38, and thus matches our assembly. The six remaining discrepancies are indels in long homopolymers. When one examines the data at loci like these, one typically sees very low quality reads (usually with quality disintegrating on one side of the homopolymer). Thus it is quite possible that these discrepancies are due to assembly errors.

This comparison also displays two captured gaps in the assembly, one of size 46 bases (as measured by the finished sequence), and captured by read pairs, and the other of size 1765 bases, and not captured by read pairs. The short gap is abutted by low complexity sequence. For the long gap, there is a separate "standalone" contig of size 1225 bases that fits in the gap, and which perfectly matches the finished sequence, and suggesting that an improved version of the algorithm might at least place this sequence within the gap.

Example 9—Assembly Fidelity

This example considers two approaches to the assessment of human genome assembly fidelity. The first approach was to measure the properties of an assembly of a given sample by comparing to reference sequences obtained from the exact same sample. For the first approach it was necessary to have a true diploid assembly. The second approach was to measure the assembly by comparing to the human reference sequence, understanding that some differences would be due to bona fide differences between the originating samples.

Parental sequence data may also be used to assess an assembly. In particular, this could provide a direct readout on the accuracy of phase blocks in a diploid assembly. This has not been done before for human genomes, because for the two extant diploid human assemblies, the parents were not sequenced. This example had four of the Supernova assemblies, (C, E, and G in Table 1). The parents had been sequenced, and phased VCFs were available. This example allowed estimation of the phasing accuracy of these assemblies.

To do this, for each megabubble, whenever two positions were found on alternate branches that could be mapped to the same position on GRCh37, which represented different bases (a heterozygous SNP), and which was phased in the VCF, either 0 or 1 was recorded, depending on whether the "top" branch of the megabubble was assigned to the maternal or paternal allele. A sequence of all 0s or all 1s would represent perfect phasing. An evaluation counted all the "votes" (0 or 1), and counted all "wrong votes" (1 if majority=0, 0 if majority=1), and summed across all megabubbles of size ≥100 kb. The global error rate for phasing of a given assembly would be (wrong votes)/votes, noting that a "long switch" error on even a single megabubble could drive this rate up. This example did not screen out "wrong chromosome" events so that these would also contribute to the error rate (on average 50% of the time).

The observed error rates were (shown in Table 1): assembly C (HG00733, Puerto Rican) 0.089% (1368 errors); assembly E (NA24385, Ashkenazi) 0.053% (640 errors); assembly G (NA12878, European) 0.018%=(270 errors). Of the 270 errors for assembly G, 178 were in a single 2 Mb megabubble, and represented a "long switch" error. Similarly of the 640 errors for assembly E, 556 were in two events. For assembly G, 97% of megabubbles were free of detected phasing errors, and 96% for assembly E, whereas this number was only 66% for assembly C, suggesting inaccuracy in the phasing truth data for the Puerto Rican sample. Overall, the data suggests that phasing errors consists of very rare long switch events (perhaps 1-2 per assembly), together with isolated short switch events occurring in a few percent of megabubbles.

Reference sample comparison is described below. Measurements of assembly completeness were highly dependent on the size floor that is used. This example chose an arbitrary cutoff of 10 kb, ignoring scaffolds shorter than this size. To measure the relative completeness of different assemblies, this example chose count k-mers, because although this approach was imperfect, it was simple and thus relatively straightforward to interpret. Moreover, the method would correctly penalize for regions in an assembly that had a very high error rate. This example used K=100, balancing between two considerations. First it was thought particularly important that the fraction of duplicate k-mers be small, as the analysis would be blind to them. The fraction of duplicate k-mers in GRCh37 is 2.3%. Second, this example did not want to lose too many k-mers to polymorphism. Assuming a polymorphism rate of 1/1000, one would expect about 10% of k-mers would be missing because of sample-to-sample differences.

This example then defined the completeness of a human assembly to be the fraction of the non-duplicate k-mers in GRCh37 that occur in the assembly. Coverage of haploid assemblies is labeled as such (Table 1). For Supernova assemblies, this example could either compute their haploid coverage (using output type pseudohap) or their diploid coverage (using output type pseudohap2). This example did not use k-mers in the raw graph although that would have yielded a somewhat higher coverage. For the YH assembly, because there was no direct way to divide the assembly into haplotypes, this example used the entire assembly and reported the coverage statistic as diploid.

This example then assessed misassemblies. To do this, for a given assembly, and for fixed sizes (1 Mb, 10 Mb), the study selected all scaffold segments of the given size in the assembly whose end k-mers occurred exactly once in the reference sequence. This example reported the fraction of such segments for which the end k-mer positions are consistent, meaning specifically that they lie on the same chromosome, in the correct order and orientation, and define a fragment whose length is within 10% of the fixed size. This example excluded cases that bridged a gap of size 100 or more in the reference, as these gap sizes could be inaccurate or polymorphic.

Example 10—Computational Benefits

The aforementioned examples show embodiments of the technologies disclosed herein. In contrast to the existing technologies, such as those provided by PacBio, the examples herein started with different data types resulting from the underlying barcode technology. As such, the examples considered less noisy data, resulting in lower error rate and higher accuracy.

The technologies disclosed herein include a preliminary filtering step. The filtering step comprises utilization of base quality scores from the sequencer. Further, the step considers k-mers that occur more than once. The step further comprises utilization of the barcodes, wherein each k-mer must be seen arising from two distinct barcodes. A great advantage of the filtering step was the ability to reduce the amount of starting data by at least two-fold to an order of magnitude.

Technologies disclosed herein utilize simple data structures: vectors of vectors. Vectorized computations allowed for faster computing time. When sparse vectors/matrices arise in some applications, vectorized computations are easier to be manipulated for much reduction in computing time.

Technologies disclosed herein utilize loops to employ CPUs, rather than GPUs, for massively parallel computing. In some applications GPUs are employed. Certain implementations include both CUPs and GUPs are employed. The merits of parallel computing allow for reduced computing time.

Technologies disclosed herein utilize lossless random access compression applied to each record of the quality scores and the paths through the graphs (including sequences and edges). The merits of compression allow for less required memory for the analysis and less required storage for holding data or analysis outcomes.

In contrast to the FALCON assembler from PacBio, these examples reduced computing time by 180-fold and lowed the memory utilization by 21-fold.

Example 11—Computing Architecture

Figure 9:
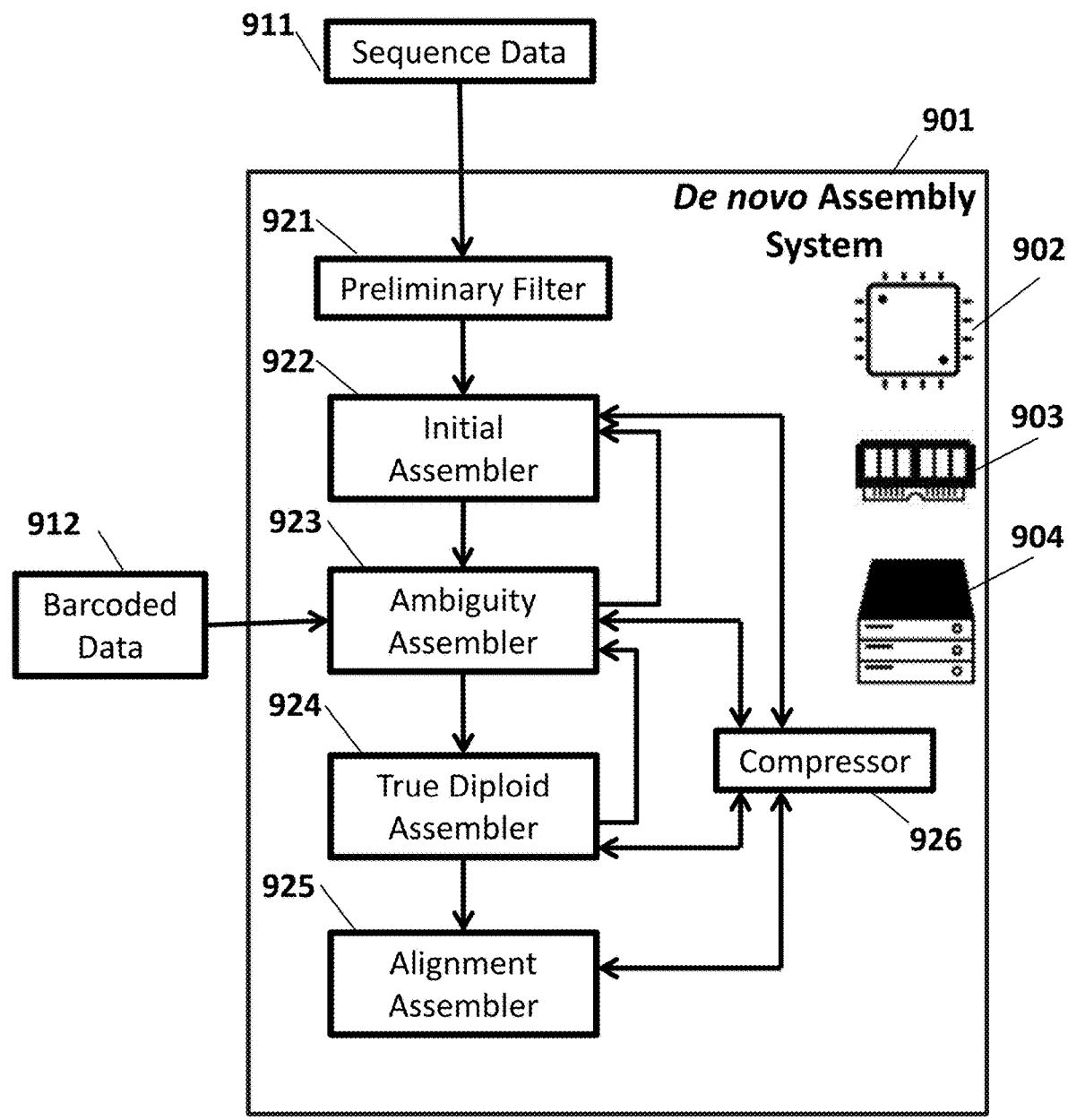
FIG. 9 shows a non-limiting example of computing architecture of a de novo assembler.

FIG. 9 shows a non-limiting block diagram of a de novo assembly system 901 as described herein. The system may comprise at least one CPU 902, memory 903, and storage 904. The computing architecture functions as follows. A set of sequence data 911 is supplied to the de novo assembly system 901. A preliminary filter 921 utilizes base quality scores from a sequencer used to generate the short-read sequence data, and utilizes k-mers for preprocessing. Then, an assembler 922 creates an initial assembly graph. This initial assembly amounts to a "rough sketch" assembly and temporarily ignores areas of unresolved complexity, e.g., regions that may be ambiguous upon first glance, thus, preserving computing power.

The output of the initial assembler 922 is fed to an ambiguity assembler 923. Areas of ambiguity may then be further processed by employing the barcoded sequencing data 912 to create an accurate assembly of the areas of ambiguity. The output of the ambiguity processor 923 includes k-mers derived from sequencing reads created during the assembly process to be addressable to a certain chromosome, cell, population, haplotype, etc. An assembler 924 is employed to assembler true diploid, based on steps shown in FIG. 2. The barcoded reads are placed back on the assembly and loci are identified whose exact sequence is not known with certainty, and so marked. A final assembler 925 is used to align the global assembly graph with respect to a reference sequence. Edges are aligned individually. When there are inconsistent alignments, the inconsistency is resolved by aligning the concatenations of these edges.

The system may further comprise a lossless random access compressor 926 that compresses one or more records of the quality scores and paths through the graph.

In various applications, the filter (921), assemblers (922, 923, 924 and 925), and compressor (926) may be implemented in hardware, or software, or a combination thereof. The filter (921), assemblers (922, 923, 924 and 925), and compressor (926) can, individually or together, be configured to execute one or more functionalities disclosed herein. Some implementations may interchange the execution order of the filter (921), assemblers (922, 923, 924 and 925), and compressor (926), or may integrate two or more them into a single execution module.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A computer-implemented method of de novo genome assembly for nucleic acid sequence data generated from a nucleic acid sample of an organism, the method comprising:
   (a) generating, by one or more computers, an initial assembly based on short-read sequence data, the initial assembly comprising one or more areas of unresolved sequence ambiguity, wherein the short-read sequence data is derived from longer starting sequences from the nucleic acid sequence data and is tagged to preserve long-range sequence context for the organism such that a subset of the short-read sequence data derived from a common starting sequence share one or more common tags;
   (b) generating, by the one or more computers, a plurality of local assemblies based on the initial assembly by utilizing the one or more common tags to resolve the one or more areas of unresolved sequence ambiguity, wherein the plurality of local assemblies is generated by:
      (i) using the initial assembly as an interim reference;
      (ii) identifying edges of an unambiguous sequence;
      (iii) identifying neighboring edges sharing a number of the one or more common tags above a threshold number of common tags; and
      (iv) bringing together edges of the unambiguous sequence with the neighboring edges identified;
   (c) generating, by the one or more computers, a global assembly based on the plurality of local assemblies;
   (d) cleaning, by the one or more computers, the global assembly by removing sequence data inconsistent with the long-range sequence context indicated by the one or more common tags; and
   (e) generating, by the one or more computers, a phased genome assembly based on the global assembly by utilizing the one or more common tags to separate a phased nucleotide sequence;
wherein the phased genome assembly is achieved without alignment to a reference sequence or any independently generated genome sequence.

2. The method of claim 1, wherein the phased genome assembly is for a diploid genome.

3. The method of claim 1, wherein the short-read sequence data is generated from a single library.

4. The method of claim 1, wherein the short-read sequence data results in 50× or less coverage of a genome of the organism.

5. The method of claim 1, wherein the short-read sequence data is tagged to preserve context over a starting sequence 2×-1000× longer than reads from the short-read sequence data.

6. The method of claim 1, wherein the initial assembly is an initial assembly graph.

7. The method of claim 6, wherein the initial assembly graph is generated by:
   (a) identifying a plurality of k-mers that have a high probability of being present in a genome of the organism;
   (b) using the one or more common tags to filter the plurality of k-mers based on a number of starting sequences each k-mer occurs in; and
   (c) bringing together k-mers in the plurality of k-mers sharing a common l-mer to form an initial assembly, wherein $1<k$.

8. The method of claim 7, further comprising applying, by the one or more computers, a preliminary filter prior to generating the initial assembly, wherein the preliminary filter comprises:
   (a) utilization of base quality scores from a sequencer used to generate the short-read sequence data, and
   (b) utilization of k-mers that occur more than once and the one or more common tags, such that each k-mer must be seen arising from two distinct common tags.

9. The method of claim 8, further comprising applying, by the one or more computers, lossless random access compression to each record of the base quality scores and paths through the graph.

10. The method of claim 7, wherein method further comprises revising, by the one or more computers, the initial assembly graph by:
    (a) eliminating the one or more areas of unresolved sequence ambiguity based on a number of reads available for each option within an area of unresolved sequence ambiguity; and
    (b) filling in gaps in the initial assembly graph by consulting the short-read sequence data.

11. The method of claim 7, wherein k is between 24 and 96.

12. The method of claim 7, wherein the global assembly is generated by:
    (a) identifying a plurality of z-mers in the plurality of local assemblies that have a high probability of being present in a genome of the organism, wherein $z>k$; and (b) bringing together z-mers of the plurality of z-mers in the plurality of local assemblies.

13. The method of claim 12, wherein z is between 100 and 300.

14. The method of claim 1, wherein the short-read sequence data is generated from less than 10 ng of DNA input material.

15. The method of claim 14, wherein the short-read sequence data is generated from less than 2 ng of DNA input material.

16. The method of claim 1, wherein the phased genome assembly is completed in less than 60 minutes.

17. The method of claim 1, wherein the phased genome assembly is completed in less than 20 minutes.

18. The method of claim 1, wherein the nucleic acid sequence data is whole genome sequence data and the phased genome assembly is a whole genome assembly, wherein the nucleic acid sequence is a deoxyribonucleic acid (DNA) sequence.

19. The method of claim 1, where the short-read sequence data is tagged to preserve long-range sequence context over a starting sequence of 10 kilobases (kb) to 5 megabases (Mb).

20. A computer-implemented system comprising: a digital processing device comprising: at least one processor, an operating system configured to perform executable instructions, a memory, and a computer program including instructions executable by the digital processing device to create a de novo genome assembly application for nucleic acid sequence data generated from a nucleic acid sample of an organism, wherein the de novo genome assembly application is programmed to:
  (a) generate an initial assembly based on short-read sequence data, the initial assembly comprising one or more areas of unresolved sequence ambiguity, wherein the short-read sequence data is derived from longer starting sequences from the nucleic acid sequence data and is tagged to preserve long-range sequence context for the organism such that a subset of the short-read sequence data derived from a common starting sequence share one or more common tags;
  (b) generate a plurality of local assemblies based on the initial assembly by utilizing the one or more common tags to resolve the one or more areas of unresolved sequence ambiguity, wherein the plurality of local assemblies is generated by:
    (i) using the initial assembly as an interim reference;
    (ii) identifying edges of an unambiguous sequence;
    (iii) identifying neighboring edges sharing a number of the one or more common tags above a threshold number of common tags; and
    (iv) bringing together edges of the unambiguous sequence with the neighboring edges identified;
  (c) generate a global assembly based on the plurality of local assemblies;
  (d) clean the global assembly by removing sequence data inconsistent with the long-range sequence context indicated by the one or more common tags; and
  (e) generate a phased genome assembly based on the global assembly by utilizing the one or more common tags to separate a homologous phased nucleotide sequence,
wherein the de novo genome assembly application is programmed to achieve the phased genome assembly without alignment to a reference sequence or any independently generated genome sequence.

21. The system of claim 20, wherein the memory comprises less than 512 GB of storage.

22. The system of claim 21, wherein the memory comprises less than 60 GB of storage.

23. The system of claim 20, wherein the phased genome assembly is completed in less than 20 minutes.

24. The system of claim 23, wherein the memory comprises less than 512 GB of storage.

25. The system of claim 24, wherein the memory comprises less than 60 GB of storage.

26. The system of claim 20, wherein the digital processing device occupies one cubic foot or less of physical space.

27. The system of claim 20, wherein the de novo genome assembly application is programmed to complete the phased genome assembly in less than 60 minutes.

28. Non-transitory computer-readable storage media encoded with a computer program including instructions executable by a processing device to create a de novo genome assembly application for nucleic acid sequence data generated from a nucleic acid sample of an organism, wherein the de novo genome assembly application is programmed to:
  (a) generate an initial assembly based on short-read sequence data, the initial assembly comprising one or more areas of unresolved sequence ambiguity, wherein the short-read sequence data is derived from longer starting sequences from the nucleic acid sequence data and is tagged to preserve long-range sequence context for the organism such that a subset of the short-read sequence data derived from a common starting sequence share one or more common tags;
  (b) generate a plurality of local assemblies based on the initial assembly by utilizing the one or more common tags to resolve the one or more areas of unresolved sequence ambiguity, wherein the plurality of local assemblies is generated by:
    (i) using the initial assembly as an interim reference;
    (ii) identifying edges of an unambiguous sequence;
    (iii) identifying neighboring edges sharing a number of the one or more common tags above a threshold number of common tags; and
    (iv) bringing together edges of the unambiguous sequence with the neighboring edges identified;
  (c) generate a global assembly based on the plurality of local assemblies;
  (d) clean the global assembly by removing sequence data inconsistent with the long-range sequence context indicated by the one or more common tags; and
  (e) generate a phased genome assembly based on the global assembly by utilizing the one or more common tags to separate a homologous phased nucleotide sequence,
wherein the de novo genome assembly application is programmed to achieve the phased genome assembly without alignment to a reference sequence or any independently generated genome sequence.

29. The non-transitory computer-readable storage media of claim 28, wherein the de novo genome assembly application is programmed to complete the phased genome assembly in less than 60 minutes.

\* \* \* \* \*